US011786486B2

(12) United States Patent
Pinnamaneni et al.

(10) Patent No.: US 11,786,486 B2
(45) Date of Patent: Oct. 17, 2023

(54) PHARMACEUTICAL COMPOSITIONS COMPRISING 2,3,5-TRIMETHYL-6-NONYLCYCLOHEXA-2,5-DIENE-1,4-DIONE

(71) Applicant: PTC THERAPEUTICS, INC., South Plainfield, NJ (US)

(72) Inventors: Swathi Pinnamaneni, East Brunswick, NJ (US); Mandar V. Dali, Bridgewater, NJ (US); Dhaval Patel, Bridgewater, NJ (US); Akm Nasir Uddin, Somerset, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 17/861,124

(22) Filed: Jul. 8, 2022

(65) Prior Publication Data

US 2023/0022538 A1    Jan. 26, 2023

Related U.S. Application Data

(60) Provisional application No. 63/219,784, filed on Jul. 8, 2021.

(51) Int. Cl.
    *A61K 31/122* (2006.01)
    *A61K 31/047* (2006.01)
    *A61K 36/63* (2006.01)
    *A61K 36/899* (2006.01)

(52) U.S. Cl.
    CPC .......... *A61K 31/122* (2013.01); *A61K 31/047* (2013.01); *A61K 36/63* (2013.01); *A61K 36/899* (2013.01)

(58) Field of Classification Search
    None
    See application file for complete search history.

(56) References Cited

U.S. PATENT DOCUMENTS

| | | |
|---|---|---|
| 5,059,627 A | 10/1991 | Goto et al. |
| 5,801,159 A | 9/1998 | Miller et al. |
| 6,232,060 B1 | 5/2001 | Miller et al. |
| 6,271,266 B1 | 8/2001 | Miyamoto et al. |
| 6,608,196 B2 | 8/2003 | Wang et al. |
| 6,653,346 B1 | 11/2003 | Wang et al. |
| 7,432,305 B2 | 10/2008 | Miller et al. |
| 8,653,144 B2 | 2/2014 | Miller et al. |
| 9,399,612 B2 | 7/2016 | Miller |
| 11,174,212 B2 | 11/2021 | Hinman et al. |
| 11,186,559 B2 | 11/2021 | Giannousis et al. |
| 2002/0143049 A1 | 10/2002 | Miller et al. |
| 2003/0176361 A1 | 9/2003 | Wand et al. |
| 2004/0105817 A1 | 6/2004 | Gilat et al. |
| 2005/0065099 A1 | 3/2005 | Walkinshaw et al. |
| 2006/0051844 A1 | 3/2006 | Heavner et al. |
| 2006/0281809 A1 | 12/2006 | Miller et al. |
| 2007/0072943 A1 | 3/2007 | Miller et al. |
| 2007/0225261 A1 | 9/2007 | Miller et al. |
| 2009/0291092 A1 | 11/2009 | Miller et al. |
| 2010/0010100 A1 | 1/2010 | Hinman et al. |
| 2010/0029706 A1 | 2/2010 | Miller et al. |
| 2010/0029784 A1 | 2/2010 | Hinman et al. |
| 2010/0056429 A1 | 3/2010 | Miller et al. |
| 2010/0063161 A1 | 3/2010 | Miller et al. |
| 2010/0105930 A1 | 4/2010 | Wesson et al. |
| 2010/0266591 A1 | 10/2010 | Bugelski et al. |
| 2010/0273892 A1 | 10/2010 | Miller et al. |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0101169 A1 | 4/2012 | Hawi |
| 2012/0122934 A1 | 5/2012 | Jankowski et al. |
| 2012/0122969 A1 | 5/2012 | Miller et al. |
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0345312 A1 | 12/2013 | Jankowski et al. |
| 2014/0243424 A1 | 8/2014 | Mollard et al. |
| 2014/0249332 A1 | 9/2014 | Mollard |
| 2014/0256830 A1 | 9/2014 | Hinman et al. |

(Continued)

FOREIGN PATENT DOCUMENTS

| | | |
|---|---|---|
| EP | 719552 | 7/1996 |
| WO | WO 99/61409 | 12/1999 |

(Continued)

OTHER PUBLICATIONS

Asin-Cayuela et al., "Fine-tuning the hydrophobicity of a mitochondria-targeted antioxidant", FEBS Letters, 2004, vol. 571, pp. 9-16.

Bates et al., "Methoxymetacyclophanes from 2,6-Dimethylanisole," J. of Organic Chemistry, 1991, 56(5), pp. 1696-1699.

Bieniek et al., "Tau Pathology in Frontotemporal Lobar Degeneration with C9ORF72 Hexanucleotide Repeat Expansion", Acta Neuropathol, Feb. 2013; 125(2): 289-302. doi:10.1007/s00401-012-1048-7.

Chong et al., "Tau Proteins and Tauopathies in Alzheimer's Disease," Cellular and Molecular Neurobiology (2018) 38:965-980.

Fieser et al., "Alkylation of Para Quinones with Acyl Peroxides," Journal of the American Chemical Society, Sep. 1942, 64(9), pp. 2060-2065.

He et al. "Amyotrophic Lateral Sclerosis-associated GGGGCC repeat expansion promotes Tau phosphorylation and toxicity", Neurobiology of Disease 130 (2019) 104493.

(Continued)

*Primary Examiner* — Michael Barker
(74) *Attorney, Agent, or Firm* — Squire Patton Boggs (US) LLP

(57) ABSTRACT

Disclosed herein is pharmaceutical compositions of Compound 1, and/or the hydroquinone form thereof, and methods useful for treating or suppressing a disease or disorder such as an α-synucleinpathy, a tauopathy, an autistic spectrum disorder, a pervasive developmental disorder, a liver disease, and liver damage in a subject using such pharmaceutical compositions.

29 Claims, 10 Drawing Sheets

(56) References Cited

U.S. PATENT DOCUMENTS

| | | |
|---|---|---|
| 2014/0275045 A1 | 9/2014 | Hinman et al. |
| 2014/0275054 A1 | 9/2014 | Hinman et al. |
| 2014/0377312 A1 | 12/2014 | Krumme et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2016/0024085 A1 | 1/2016 | Hinman et al. |
| 2016/0115141 A1 | 4/2016 | Hinman et al. |
| 2018/0000749 A1 | 1/2018 | Mollard et al. |
| 2018/0333389 A1 | 11/2018 | Miller |
| 2018/0362492 A1 | 12/2018 | Giannousis et al. |
| 2018/0370892 A1 | 12/2018 | Hinman et al. |
| 2019/0029975 A1 | 1/2019 | Shrader |
| 2019/0241497 A1 | 8/2019 | Hinman |
| 2019/0330159 A1 | 10/2019 | Kitano et al. |
| 2020/0121618 A1 | 4/2020 | Miller et al. |
| 2022/0106248 A1 | 4/2022 | Hinman et al. |
| 2022/0220054 A1 | 7/2022 | Hinman et al. |

FOREIGN PATENT DOCUMENTS

| | | |
|---|---|---|
| WO | WO 2007/095631 A2 | 8/2007 |
| WO | WO 2011/113018 | 9/2011 |
| WO | WO 2012/154613 | 11/2012 |
| WO | WO 2012/170773 A1 | 12/2012 |
| WO | WO 2013/006736 | 1/2013 |
| WO | WO 2013/110442 | 8/2013 |
| WO | WO 2015/183963 | 12/2015 |
| WO | WO 2016/114860 | 7/2016 |
| WO | WO 2017/123823 | 7/2017 |
| WO | WO 2018/129411 | 7/2018 |
| WO | WO 2018/191732 A1 | 10/2018 |
| WO | WO 2020/081879 A1 | 4/2020 |
| WO | WO 2020/252414 A1 | 12/2020 |
| WO | WO 2021/077034 A1 | 4/2021 |

OTHER PUBLICATIONS

Hirano et al., Neuropathology of amyotrophic lateral sclerosis and parkinsonism-dementia complex on Guam. In: Luthy L, Bischoff A, editors. Proceedings of the Fifth International Congress of Neuropathology. Amsterdam: Excerpta Medica (1966). p. 190-194; Hirano A, et al., Arch Neurol. (1966) 15:35-51.

Hubscher et al., "Total Synthesis of Naturally Occurring a-Tocopheroi. Asymmetric Alkylation and Asymmetric Epoxidation as Means to Introduce (R)-Configuration at C(2) of the Chroman Moiety", Helvetica Chimica Acta 1990, 73(4), p. 1068.

Kalayci et al., "Effect of Coenzyme O1O on ischemia and neuronal damage in an experimental traumatic brain-injury model in rats," BMC Neuroscience, Jul. 29, 2011, vol. 12, No. 75, pp. 1-7.

King et al., "Mixed tau, TDP-43 and p62 pathology in FTLD associated with a C9ORF72 repeat expansion and p.Ala239Thr MAPT(tau) variant", Acta Neuropathol, published online: Sep. 28, 2012; DOI 10.1007/s00401-012-1050-0.

Lillo et al., "Amyotrophic lateral sclerosis and frontotemporal dementia: A behavioural and cognitive continuum", Informa Healthcare, Amyotrophic Lateral Sclerosis, 2012, vol. 13, pp. 102-109; DOI: 10.3109/17482968.2011.639376.

Monte et al., "An Efficient Process for the Synthesis of y-Arylbutanals via Copper-Mediated Grignard Coupling", Organic Process Research & Development, 2001, vol. 5, pp. 267-269.

Moszczynski et al., "Pathologic Thr175 tau phosphorylation in CTE and CTE with ALS", Neurology® 2018;90:e380-e387; doi:10.1212/WNL.0000000000004899.

Muydernnan et al. "Mitochondrial dysfunction in amyotrophic lateral sclerosis—a valid pharmacological target?" British Journal of Pharmacology, 2014, vol. 171, pp. 2191-2205.

Ozalp et al., "The effect of coenzyme Q10 on venous ischemia reperfusion injury," Journal of Surgical Research, vol. 204, No. 2, May 7, 2016, pp. 304-310.

Pelter et al., "Phenolic Oxidations with Phenyliodonium Diacetate", J. Chem. Soc., Perkin Trans. 1, 1993, vol. 16, p. 1891.

Shiraishi et al., "Novel Eicosanoid Antagonists: Synthesis and Pharmacological Evaluation", Journal of Medicinal Chemistry, 1989, 32(9), p. 2214.

Shrader et al., "COQ10 Analogies Targeting Mitochondrial Impairment In Huntington's Disease," EHDN Annual Meeting: abstracts, J Neurol Neurosurg Psychiatry 2008; 79(Suppl 1); A7-A8.

Silbert et al., "Preparation of t-Butyl Peresters and Diacyl Peroxides of Aliphatic Monobasic Acids", Journal of the American Chemical Society, May 20, 1959, 81(10), p. 2364.

Sommer et al., "Stereospecific Coupling Reactions between Organolithium Reagents and Secondary Halides", J. Org. Chem., Jan. 1970, 35(1), pp. 22-25.

Thomas et al., "Repetitive Diels-Alder Reactions for the Growth of Linear Polyacenequinoid Derivatives", Journal of Organic Chemistry, 1986, 51(22), p. 4160.

Vintilescu et al., "The neurotoxic tau45-230 Fragment Accumulates in upper and Lower Motor neurons in Amyotrophic Lateral sclerosis subjects", Molecular Medicine, 2016, vol. 22, pp. 477-486; doi: 10.2119/molmed.2016.00095.

Yang et al., "Microtubule-associated tau protein positive neuronal and glial inclusions in ALS", Neurology, vol. 61, Dec. 2003, pp. 1766-1773; DOI 10.1212/01.WNL.0000099372.75786.F8.

Yang et al., "Tau protein aggregation in the frontal and entorhinal cortices as a function of aging", Developmental Brain Research, 2005, vol. 156, pp. 127-138.

Yang et al., "Widespread neuronal and glial hyperphosphorylated tau deposition in ALS with cognitive impairment", Amyotrophic Lateral Sclerosis, 2012, vol. 13 (2), pp. 178-193; DOI: 10.3109/17482968.2011.622405.

International search report and written opinion of PCT/US2022/036589 dated Nov. 7, 2022; 12 pages.

Yap et al., "Influence of lipolysis and droplet size on tocotrienol absorption from self-emulsifying formulations", International Journal of Pharmaceutics 281, Aug. 1, 2004, pp. 67-78.

Technical Data Sheet—Lauroglycol 90, Gattefossé, Specification No. 3244 / 8, Feb. 25, 2022; 4 pages.

Technical Data Sheet—Labrafac PG, Gattefossé, Specification No. 3230 / 7, Jun. 13, 2019; 3 pages.

Technical Data Sheet—Labrafac Lipophile WL 1349, Gattefossé, Specification No. 3139 /13, Feb. 14, 2022; 4 pages.

Fig. 1: Physical Stability of Selected Gelucire 44/14-Based Formulation of Compound 1 at 100 mg/g Concentration
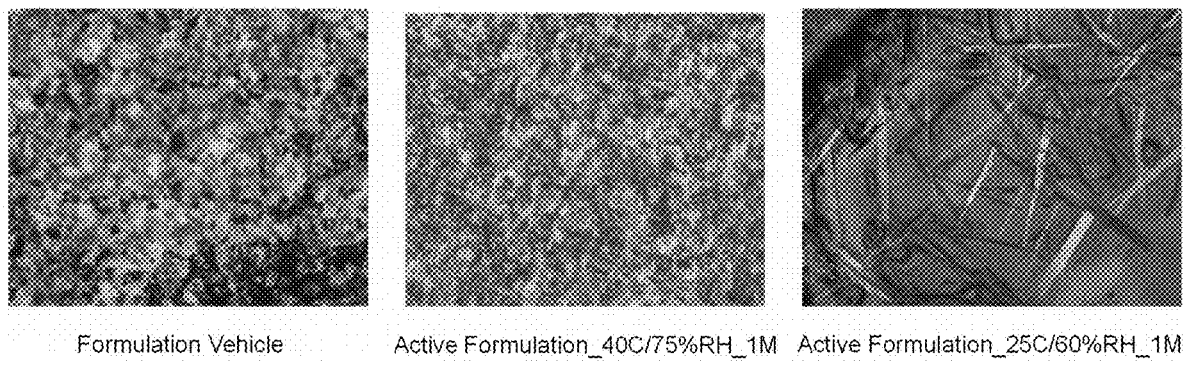

Fig. 2: Physical Stability of Selected Labrafac WL 1349-Based Formulation of Compound 1 at 100 mg/g Concentration
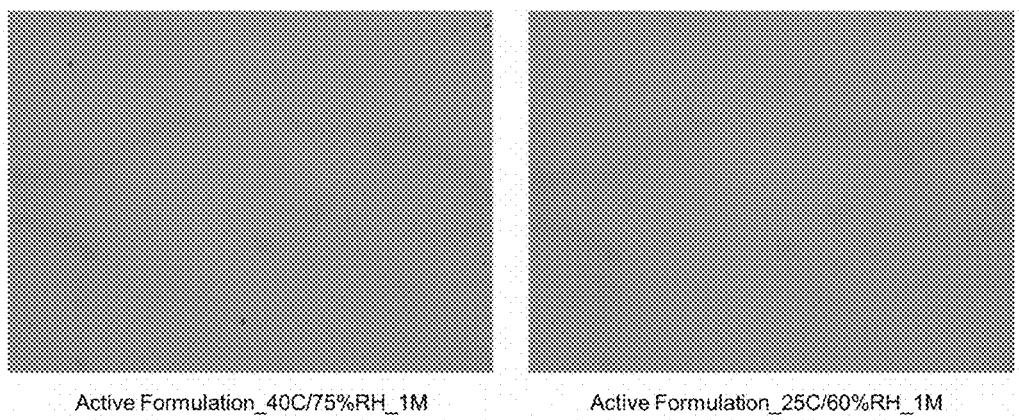

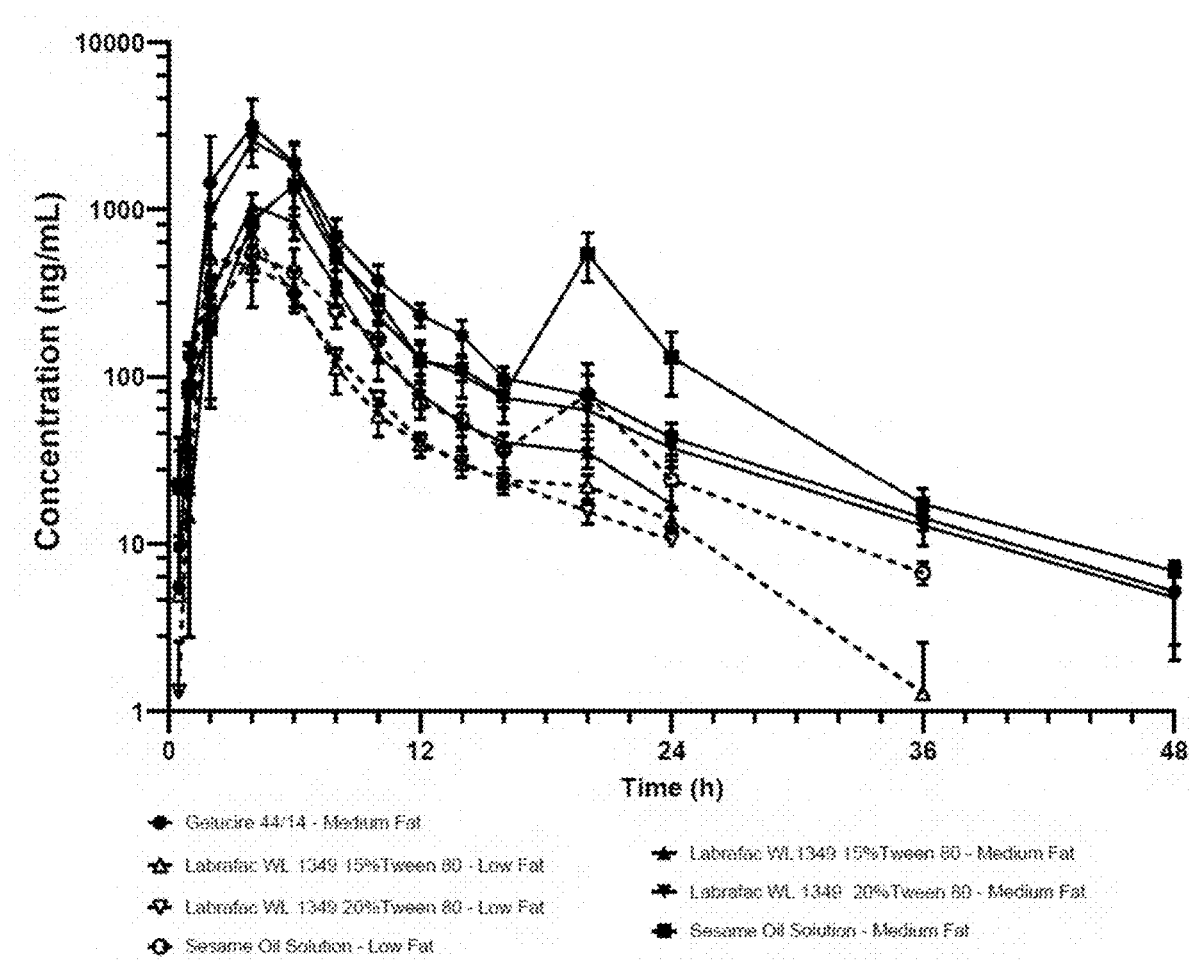
Fig. 3: Monkey PK Profiles for Sesame oil Formulation

Fig. 4a: Monkey PK Profiles for SEDDS Formulations 1-6 (All Formulations First 8 hrs, Linear Scale)
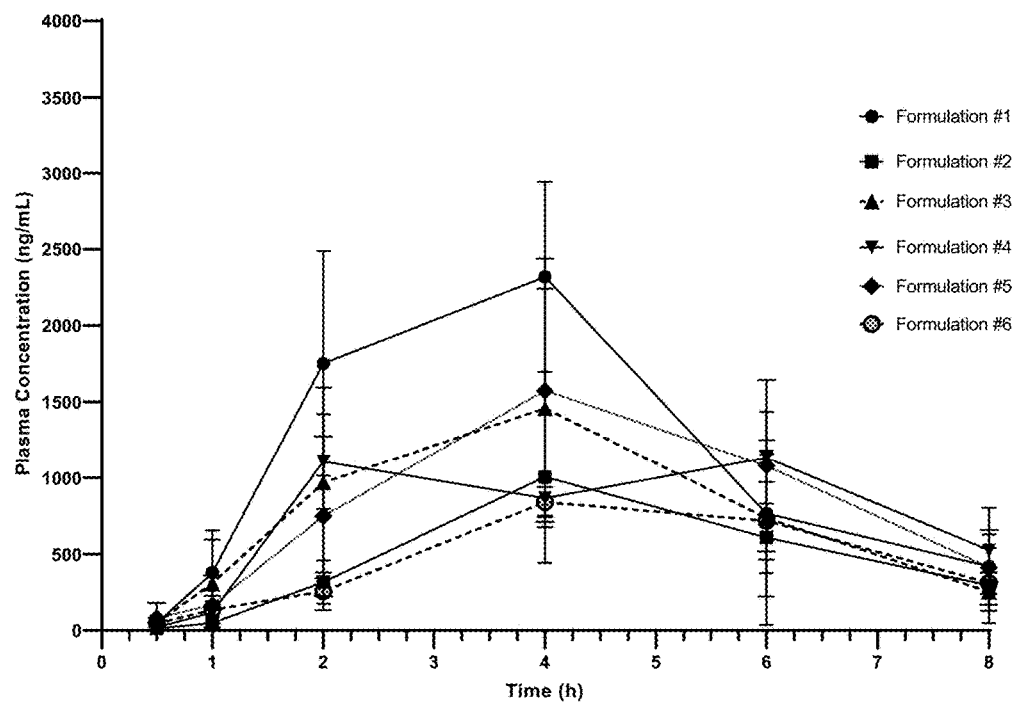

Fig. 4b: Monkey PK Profiles for SEDDS Formulations 1-6 (All Formulations First 8 hrs, Linear Scale)
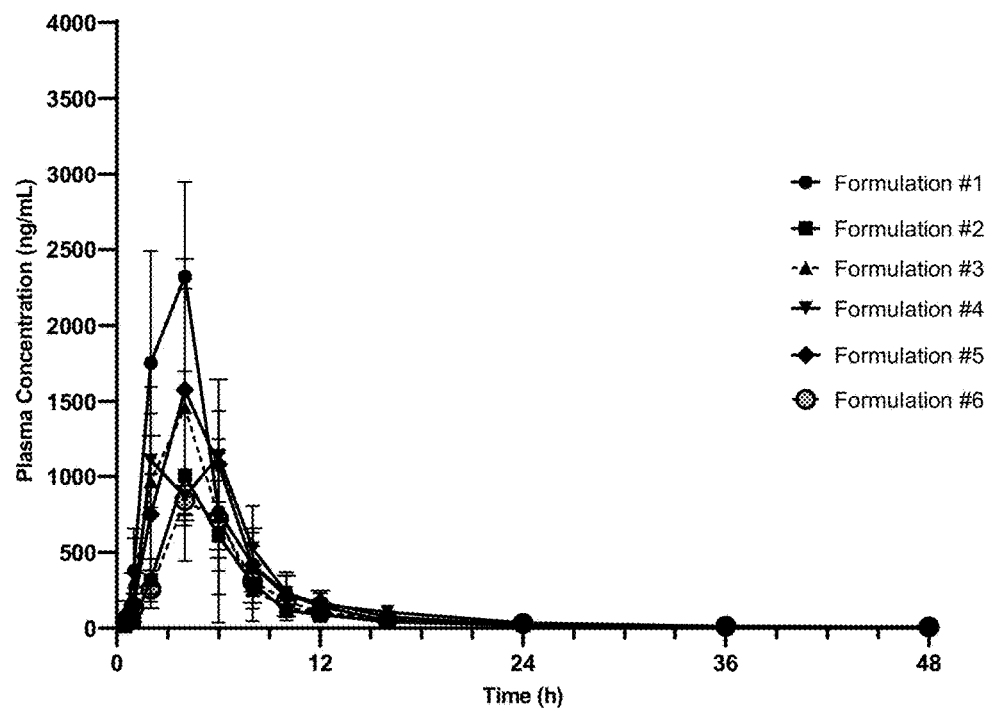

Fig. 4c: Monkey PK Profiles for SEDDS Formulations 1-6
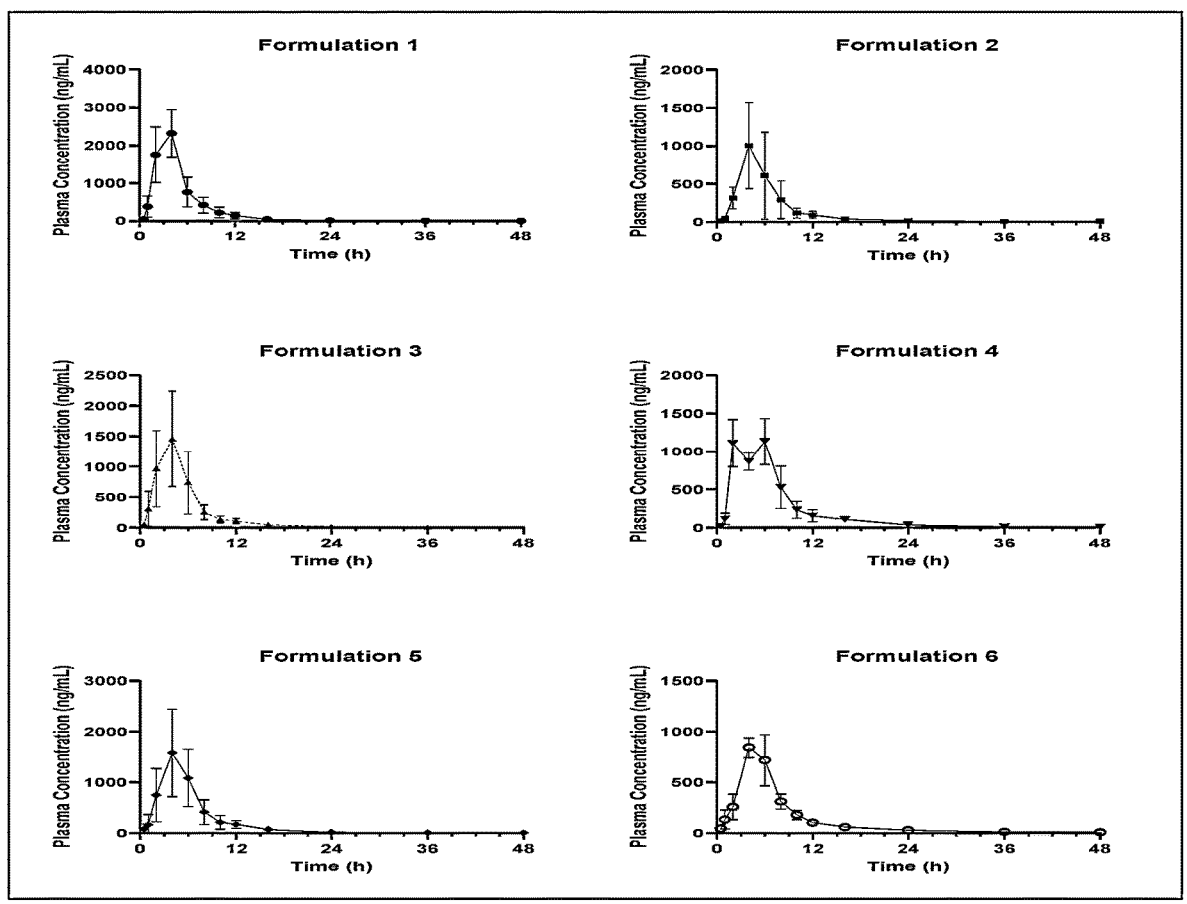

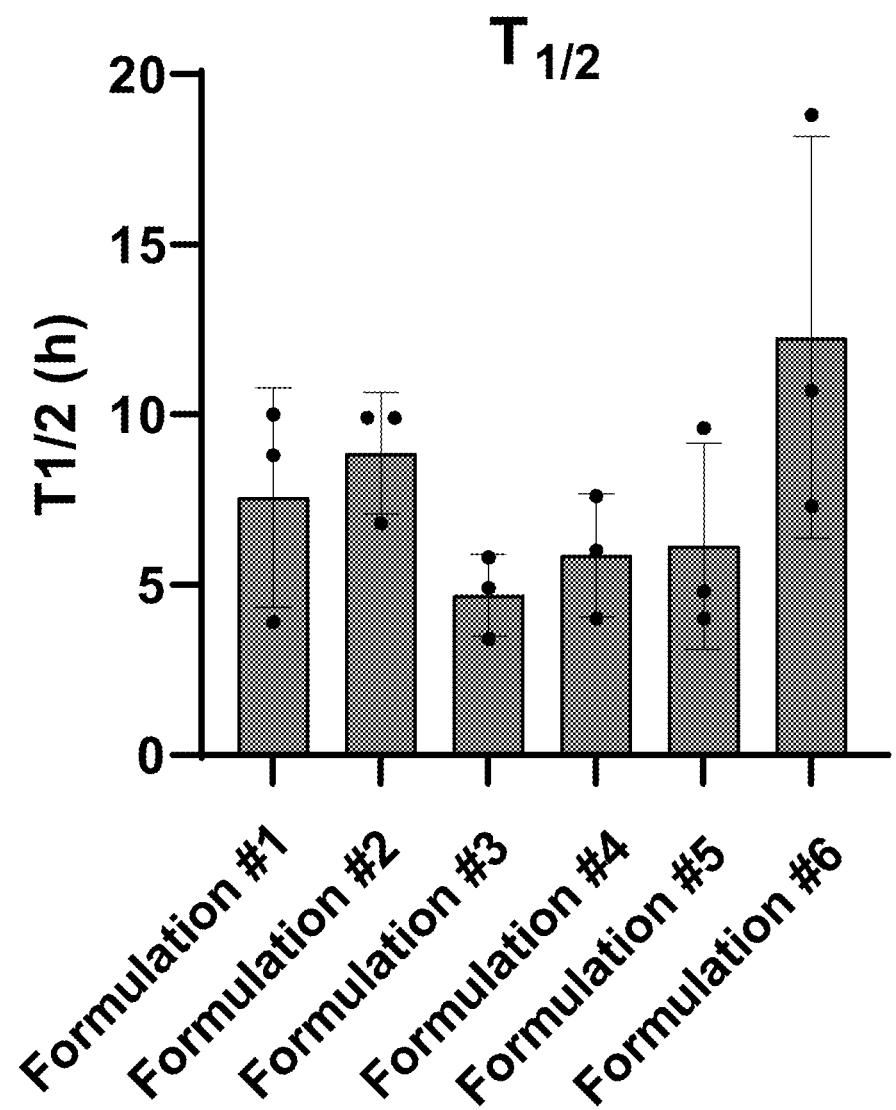
Fig. 5a: Monkey PK Parameter Comparison of SEDDS Formulations 1-6 - $T_{1/2}$

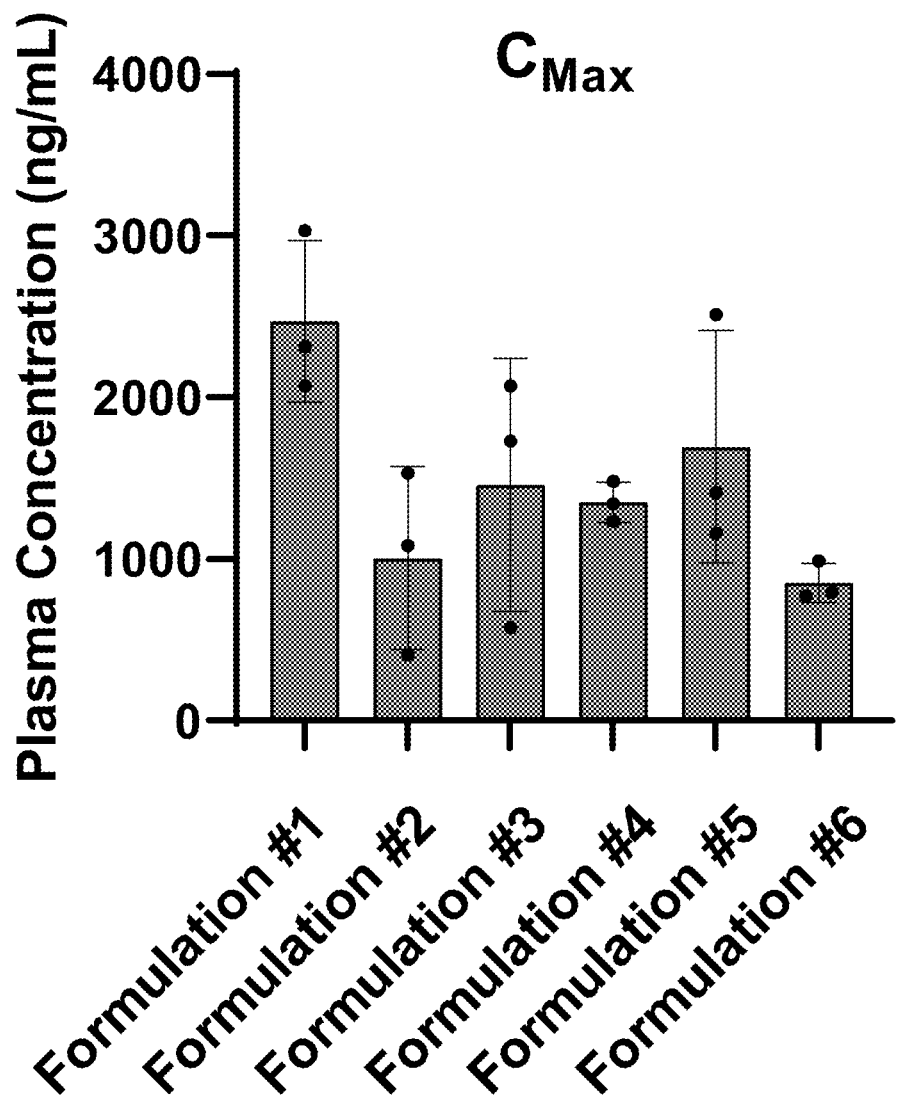
Fig. 5b: Monkey PK Parameter Comparison of the SEDDS Formulations 1-6 - $C_{Max}$

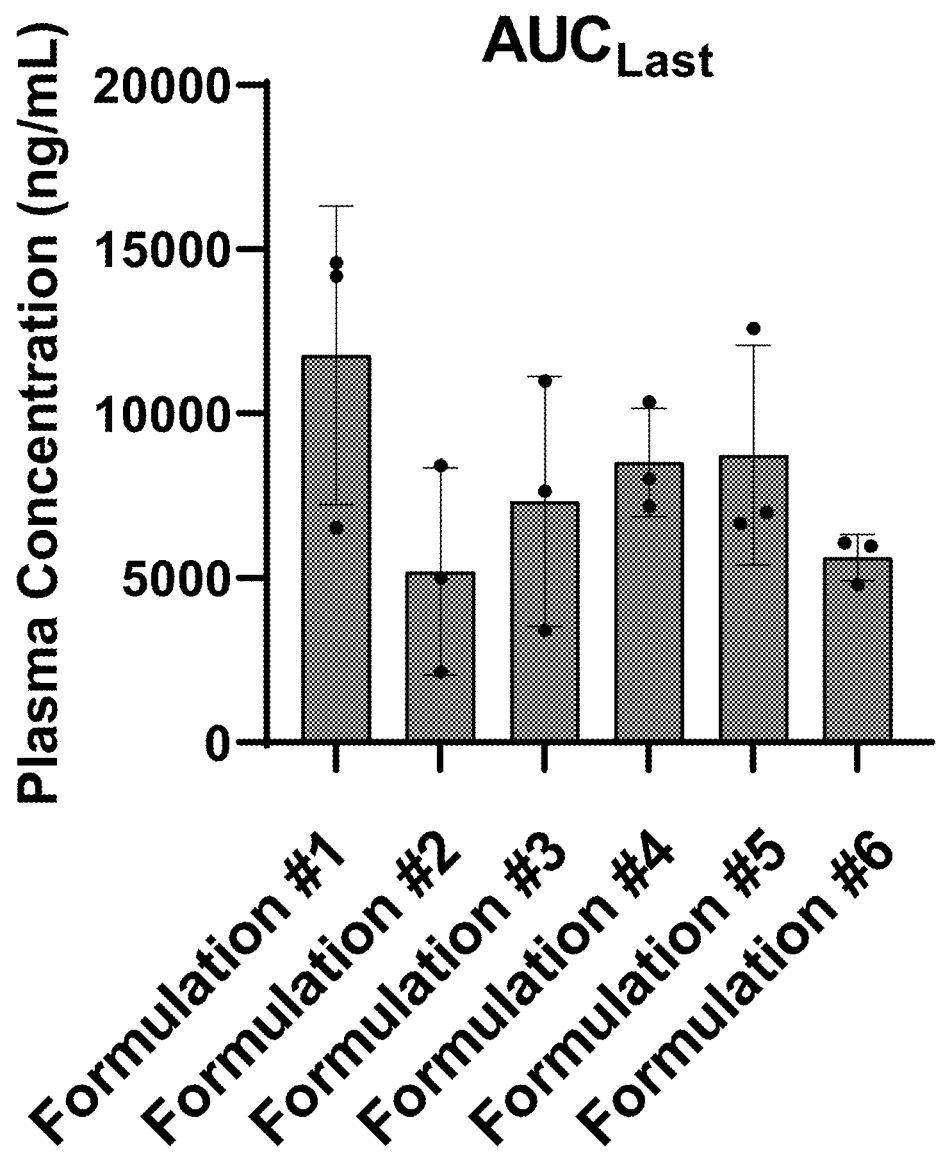
Fig. 5c: Monkey PK Parameter Comparison of the SEDDS Formulations 1-6 - $AUC_{Last}$ Fig. 6: Moisture Abstractability of the Liquid Formulation or its Components in Hard Gelatin Capsule:
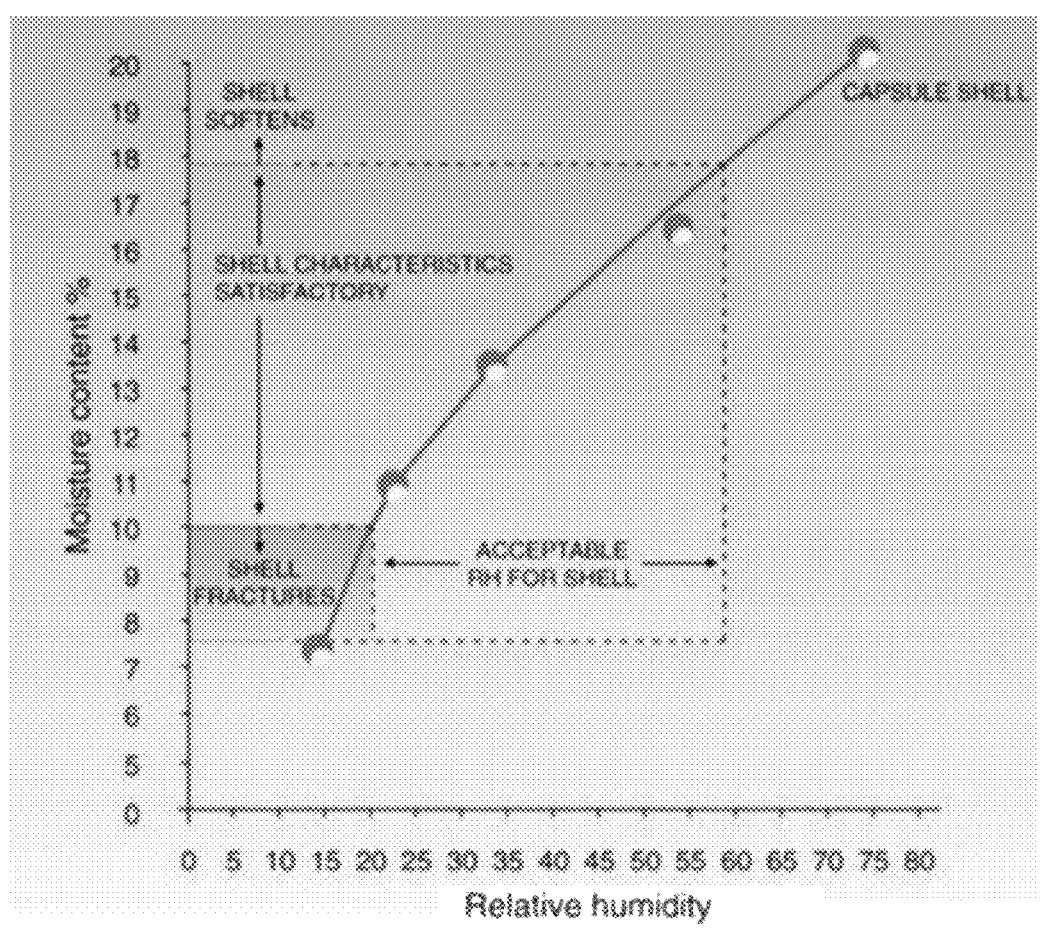

PHARMACEUTICAL COMPOSITIONS COMPRISING 2,3,5-TRIMETHYL-6-NONYLCYCLOHEXA-2,5-DIENE-1,4-DIONE

CROSS-REFERENCE TO RELATED APPLICATIONS

This application claims the benefit of U.S. Provisional Application No. 63/219,784, filed Jul. 8, 2021, the contents of which is herein incorporated by reference in its entirety.

FIELD

Provided herein is pharmaceutical composition of 2,3,5-trimethyl-6-nonylcyclohexa -2,5-diene-1,4-dione (Compound 1), and/or the hydroquinone form thereof, wherein Compound 1 is optionally provided as a hydrate, and/or solvate thereof; and methods useful for treating or suppressing a disease or disorder such as an α-synucleinpathy, a tauopathy, an autistic spectrum disorder, a pervasive developmental disorder, a liver disease, liver damage, dementia, and reperfusion injury in a subject using such pharmaceutical compositions.

BACKGROUND

U.S. Publication No. 2007/0072943 describes certain quinone compounds, pharmaceutical compositions, and methods of treating certain mitochondrial disorders. U.S. Publication No. 2010/0063161 describes the compound 2,3,5-trimethyl-6-nonylcyclohexa-2,5-diene -1,4-dione, pharmaceutical compositions, and methods for treating pervasive developmental disorders and Attention Deficit Hyperactivity Disorder (ADHD). US Publication No. US Publication No. 2020/0121618 describes the compound 2,3,5-trimethyl-6-nonylcyclohexa -2,5-diene-1,4-dione, compositions and methods useful for treating or protecting biological systems against damage caused by inflammation and/or oxidative stress. U.S. Pat. No. 11,174,212 B2 describes a polymorphic form of the compound 2,3,5-trimethyl -6-nonylcyclohexa-2,5-diene-1,4-dione, compositions and methods useful for treating or suppressing a disorder selected from the group consisting of α-synucleinopathies, tauopathies, ALS, traumatic brain injury, and reperfusion injury.

Self-emulsifying drug delivery systems (SEDDS), are lipid-based formulations mixtures of oils, surfactants, co-surfactants, and a solubilized compound. SEDDS are an important way to improve the oral absorption of highly lipophilic compounds with poor aqueous solubility. Following oral administration, SEDDS spontaneously emulsify and rapidly disperse in gastrointestinal fluids, yielding micro- or nanoemulsions containing the solubilized compound.

What are needed are pharmaceutical compositions comprising 2,3,5-trimethyl-6-nonylcyclohexa -2,5-diene-1,4-dione, for example, a SEDDS formulation. Pharmaceutical compositions provided herein show good mitigation of observed positive food effect, good bioavailability, no birefringence when stored, little or no degradation of 2,3,5-trimethyl-6-nonylcyclohexa -2,5-diene-1,4-dione during storage, and/or little or no reduction in potency.

SUMMARY

In a first aspect provided herein is a pharmaceutical composition comprising:
a) about 48 wt/wt % to about 70 wt/wt % of a pharmaceutically acceptable oil, about 12 wt/wt % to about 25 wt/wt % of a propylene glycol laurates composition, and about 8 wt/wt % to about 20 wt/wt % of a polysorbate 80;

b) about 1 wt/wt % to about 15 wt/wt % of Compound 1:

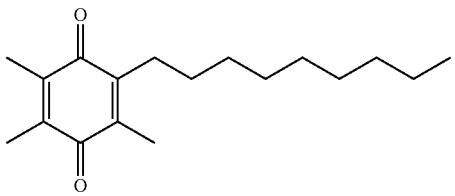 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 15 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, the propylene glycol laurates composition, the polysorbate 80, and optional flavorant total 100%.

In a second aspect provided herein is a method of preparing a pharmaceutical formulation, comprising:
step a) mixing about 48 wt/wt % to about 70 wt/wt % of the pharmaceutically acceptable oil, about 12 wt/wt % to about 25 wt/wt % of the propylene glycol laurates composition, and about 8 wt/wt % to about 20 wt/wt % of the polysorbate 80composition, and 0 wt/wt % to about 2% wt/wt % of an optional flavorant;

step b) adding about 1 wt/wt % to about 15%, of Compound 1 and/or the hydroquinone form thereof, wherein Compound 1 and/or the hydroquinone form thereof is optionally a hydrate and/or solvate thereof; to the mixture from step a) and mixing, and wherein when the Compound 1, and/or hydroquinone thereof, is in the form of a hydrate and/or solvate, then the about 1 wt/wt % to about 15 wt/wt % of Compound 1 and/or its hydroquinone, does not include the weight of any the water in the hydrate or the weight of the solvent in the solvate; and wherein the wt/wt % of Compound 1, the pharmaceutically acceptable oil, the propylene glycol laurates composition, the polysorbate 80, and optional flavorant total 100%.

In a third aspect, provided herein are methods of using the pharmaceutical composition or pharmaceutical compositions described herein. In some embodiments, the methods are useful for treating or suppressing a disease or disorder such as an α-synucleinopathy, a tauopathy, an autistic spectrum disorder, a pervasive developmental disorder, a liver disease, liver damage, dementia, and reperfusion injury in a subject using such pharmaceutical compositions.

In a fourth aspect provided herein is a pharmaceutical composition comprising:
a) about 85 wt/wt % to about 99 wt/wt % of a pharmaceutical acceptable oil;

b) about 1 wt/wt % to about 15% of Compound 1:

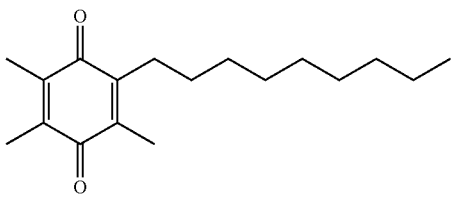 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 15 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, and optional flavorant total 100%.

In a fifth aspect, provided herein is a pharmaceutical composition comprising:

a) about 48 wt/wt % to about 70 wt/wt % of a pharmaceutically acceptable oil, about 12 wt/wt % to about 25 wt/wt % of a co-surfactant, and about 8 wt/wt % to about 20 wt/wt % of a surfactant;

b) about 1 wt/wt % to about 15 wt/wt % of Compound 1:

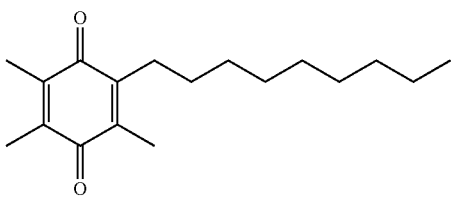 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 15 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, the surfactant, the co-surfactant, and the optional flavorant total 100%.

In a sixth aspect, provided herein is a pharmaceutical composition comprising:

a) about 65 wt/wt % to about 80 wt/wt % of a Gelucire-like oil, about 8 wt/wt % to about 10 wt/wt % of an excipient like TPGS, and about 8 wt/wt % to about 10 wt/wt % of a polysorbate 80;

b) about 1 wt/wt % to about 17 wt/wt % or about 1 wt/wt % to about 13 wt/wt % or about 1 wt/wt % to about 10 wt/wt % of Compound 1:

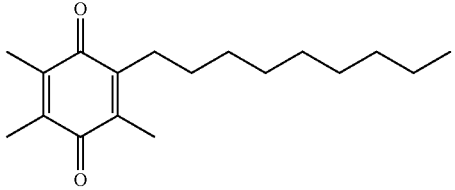 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 15 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, the surfactant, the co-surfactant, and the optional flavorant total 100%.

BRIEF DESCRIPTION OF THE DRAWINGS

FIG. 1 shows the physical stability under polarized microscope for Gelucire 44/14-based formulation of Compound 1 as described in Example 4.

FIG. 2 shows the physical stability under polarized microscope for Labrafac WL 1349-based formulation of Compound 1 as described in Example 4.

FIG. 3 shows monkey PK profiles for formulations in monkeys as described in Example 10.

FIG. 4a monkey PK profiles for SEDDS Formulations 1-6 (all formulations first 8 hrs, Linear scale) as described in Example 10.

FIG. 4b shows monkey PK profiles for SEDDS Formulations 1-6 (all formulations, Linear scale) as described in Example 10.

FIG. 4c shows monkey PK profiles for SEDDS Formulations 1-6 as described in Example 10.

FIG. 5a shows monkey PK parameter comparison of the SEDDS Formulations 1-6—$T_{1/2}$ as described in Example 10.

FIG. 5b shows monkey PK parameter comparison of the SEDDS Formulations 1-6—$C_{Max}$ as described in Example 10.

FIG. 5c shows monkey PK parameter comparison of the SEDDS Formulations 1-6—$AUC_{Last}$ as described in Example 10.

FIG. 6 shows moisture abstractability of the liquid formulation or its components in hard gelatin capsule as described in Example 11.

DETAILED DESCRIPTION

The present disclosure provides a pharmaceutical composition of Compound 1, and/or the hydroquinone form thereof, and methods useful for treating or suppressing a disease or disorder such as an α-synucleinpathy, a tauopathy, an autistic spectrum disorder, a pervasive developmental disorder, a liver disease, liver damage, dementia, and reperfusion injury in a subject using such pharmaceutical compositions.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

Use of the singular herein includes the plural and vice versa unless expressly stated to be otherwise, or obvious from the context that such is not intended. That is, "a" and "the" refer to one or more of whatever the word modifies. For example, "a therapeutic agent" includes one therapeutic agent, two therapeutic agent s, etc. Likewise, "a capsule" may refer to one, two or more capsules, and "the disease" may mean one disease or a plurality of diseases. By the same token, words such as, without limitation, "capsules" and "therapeutic agents" would refer to one capsule or therapeutic agent as well as to a plurality of capsules or therapeutic agents, unless, again, it is expressly stated or obvious from the context that such is not intended.

As used herein, unless specifically defined otherwise, any words of approximation such as without limitation, "about," "essentially," "substantially," when used in connection with various terms such as temperatures, doses, amounts, or weight percent of ingredients of a composition or a dosage form, mean e.g. a temperature, dose, amount, or weight percent that is recognized by those of ordinary skill in the art to provide an effect equivalent to that obtained from the specified temperature dose, amount, or weight percent. Specifically, the terms "about" and "approximately," when used in this context, contemplate a temperature, dose, amount, or weight percent, etc. within 15%, within 10%, within 5%, within 4%, within 3%, within 2%, within 1%, or within 0.5% of the specified temperature, dose, amount, or weight percent, etc. In addition, any of the embodiments herein, where ranges or numbers are expressed with "about," i.e. "about 48 wt/wt % to about 70 wt/wt %," can be replaced with a range or number that does not recite "about," i.e. "48 wt/wt % to 70 wt/wt %."

As used herein, any ranges presented are inclusive of the end-points. For example, "a temperature between 10° C. and 30° C." or "a temperature from 10° C. to 30° C." includes 10° C. and 30° C., as well as any specific temperature in between. Similarly, a temperature of 20° C. ±10° C. would cover the same range as "a temperature between 10° C. and 30° C."

"Alpha-synuclein" and "α-synuclein" are used interchangeably herein.

As used herein "birefringent crystals" refers to non-cubic crystals.

"Hydroquinone form" indicates the form of the compound when a two electron reduction of the quinone ring is effected, providing a net conversion of the two oxo groups to two hydroxy groups. For example, the hydroquinone form of the quinone compound:

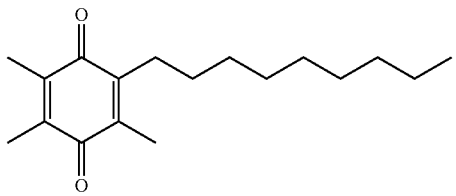 [SMILES: CCCCCCCCCC1=C(C)C(=O)C(C)=C(C)C1=O]

is the following:

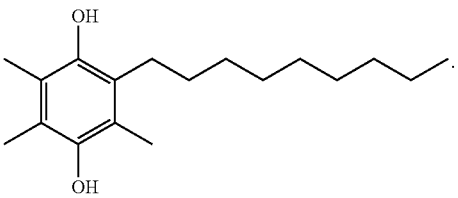 [SMILES: CCCCCCCCCc1c(C)c(O)c(C)c(C)c1O]

As used herein, "initial potency" is measured on the day the pharmaceutical composition is prepared and before it is stored on the same day as it is prepared.

As used herein, "initial total impurity level" is measured on the day the pharmaceutical composition is prepared and before it is stored, on the same day as it is prepared.

As used herein, "initial degradation level" is measured on the day the pharmaceutical composition is prepared and before it is stored on the same day as it is prepared.

As used herein, "Gelucire-like oil" refers to a composition comprising a small fraction of mono, di- and triglycerides and mainly PEG-32 (MW 1500) mono and diesters of lauric acid (C12). In some or any embodiments, the Gelucire-like oil refers to a composition consisting of a small fraction of mono, di- and triglycerides and mainly PEG-32 (MW 1500) mono and diesters of lauric acid ($C_{12}$). In some or any embodiments, the Gelucire-like oil is Gelucire 44/14.

As used herein "Labrafac-like oil" refers to an oil of medium chain triglyceride of fractionated vegetable $C_8$ and $C_{10}$ fatty acids (mainly fractionated coconut oil or palm kernel oil) with an HLB of 1. In some embodiments, Labrafac brand oil can be replaced with another oil comprising medium-chain triglycerides. In some or any embodiments, Labrafac-like oil means Labrafac WL 1349 (alternatively named Labrafac Lipophile WL 1349) or Labrafac PG. In some or any embodiments, Labrafac-like oil means Labrafac WL 1349. In some or any embodiments, Labrafac-like oil means Labrafac PG.

As used herein "propylene glycol laurates composition" refers to a composition comprising propylene glycol mono- and di-esters of lauric acid ($C_{12}$), mainly composed of monoesters and a small fraction of di-esters with HLB value 3 and can be used as a nonionic water-insoluble co-surfactant. In some embodiments, the propylene glycol laurates composition consists of propylene glycol mono-and di-esters of lauric acid ($C_{12}$), mainly composed of monoesters and a small fraction of di-esters. In some embodiments, the propylene glycol laurates composition is Lauroglycol 90. In other embodiments, the skilled person would recognize that Lauroglycol 90 can be replaced with another propylene glycol laurates composition, including, for example Capmul PG-12.

As used herein "polysorbate 80," refers to polyoxyethylene sorbitan monooleate containing 20 units of oxyethylene, which are hydrophilic, hygroscopic, nonionic surfactants that can be used as an emulsifying agent. In some embodiments, the polysorbate is Tween 80. In other embodiments, the skilled person would recognize that Tween 80 can be replaced with another polysorbate 80.

As used herein "Low-fat food for Testing" refers, in some embodiments, to food having 11.4% fat (by calories); in some embodiments, 15% fat (by calories). One example is provided in Example 10. A preparation of a "Low-fat food for Testing" is provided in Example 13a. "Low-fat food for Testing" may be provided as a single food item or may be in the form a meal.

As used herein "Medium-fat food for Testing" refers, in some embodiments, to food having 37.9% fat (by calories); in some embodiments, 38% fat (by calories). One example is provided in Example 10. A preparation of a "Medium-fat food for Testing" is provided in Example 13b. "Medium-fat food for Testing" may be provided as a single food item or may be in the form a meal.

As used herein "Low-fat food" refers to food having 25% fat or less (by calories), about 100-125 kcal or less (based on a 400-500 kcal total meal), in some embodiments 11.4% fat (by calories); in some embodiments, 15% fat (by calories). "Low-fat food" may be provided as a single food item or may be in the form a meal.

As used herein "Medium-fat food" refers to food having 25-50% fat (by calories), in some embodiments, 37.9% fat (by calories); in some embodiments, 38% fat (by calories). One example is provided in paragraph [00213] which immediately follows Table 22. Another example is provided in Example 13b. "Medium-fat food" may be provided as a single food item or may be in the form a meal.

As used herein "High-fat food" refers to food having 50% fat or more (by calories), about 500-600 kcal or more (based on a 800-1000 kcal total meal). "High-fat food" may be provided as a single food item or may be in the form a meal.

The term "pharmaceutically acceptable oil" as used herein a GMP grade oil that can be consumed orally by humans. In some embodiments, the pharmaceutically acceptable oil comprises medium-chain triglycerides. In some embodiments, the pharmaceutically acceptable oil is one that solubilizes Compound 1 at room temperature. In some embodiments, the pharmaceutically acceptable oil is selected from one or more of the group consisting of: a Labrafac-like oil (including Labrafac WL 1349 and Labrafac PG), sesame oil, cottonseed oil, soybean oil, olive oil, and corn oil. In some embodiments, the pharmaceutically acceptable oil is selected from one or more of the group consisting of: a Labrafac-like oil (including Labrafac WL 1349 and Labrafac PG), cottonseed oil, soybean oil, olive oil, and corn oil. In some embodiments, the pharmaceutically acceptable oil is selected from one or more of the group consisting of: a Labrafac-like oil (including Labrafac WL 1349 and Labrafac PG), sesame oil, cottonseed oil, soybean oil, and corn oil. In some embodiments, the pharmaceutically acceptable oil is selected from one or more of the group consisting of: a Labrafac-like oil (including Labrafac WL 1349 and Labrafac PG), cottonseed oil, soybean oil, and corn oil. In some or any embodiments, one pharmaceutically acceptable oil is selected.

As used herein, potency=(100%−total impurities by HPLC)×(100% −water content %−total residual solvent %−Residue on ignition %). Potency may be calculated as follows (% area purity by HPLC/100)*(100−% wt/wt water content (KF)−% wt/wt residual solvents−% wt/wt=residue on ignition (ROI)). In various embodiments, the potency of the 2,3,5-trimethyl-6-nonylcyclohexa-2,5-diene-1,4-dione is at least about 95%, at least about 96%, at least about 97%, at least about 98%, at least about 99%, or at least about 99.5%.

As sued herein "solvate" refers to a compound described herein that further includes a stoichiometric or non-stoichiometric amount of solvent bound by non-covalent intermolecular forces. Where the solvent is water, the solvate is a hydrate.

As used herein, the term "formulate" refers to the preparation of a drug, e.g., Compound 1, in a form suitable for oral or transdermal administration to a mammalian patient, in some embodiments, a human. Thus, "formulation" can include the addition of pharmaceutically acceptable excipients, diluents, or carriers.

A pharmaceutical composition can comprise a unit dose formulation, where the unit dose is a dose sufficient to have a therapeutic effect.

By "stable pharmaceutical composition" is meant any pharmaceutical composition having sufficient stability to have utility as a pharmaceutical product. In some embodiments, a stable pharmaceutical composition has sufficient stability to allow storage at a convenient temperature, in some embodiments, between −20° C. and 40° C., in some embodiments, about 2° C. to about 30° C., for a reasonable period of time, e.g., the shelf-life of the product which can be as short as one month but is typically six months or longer, in some embodiments, one year or longer, in some embodiments, twenty-four months or longer, and in some embodiments, thirty-six months or longer. The shelf-life or expiration can be that amount of time where the active ingredient degrades to a point below 90% purity. For purposes of the present description stable pharmaceutical composition includes reference to pharmaceutical compositions with specific ranges of impurities as described herein. In some embodiments, a stable pharmaceutical composition is one which has minimal degradation of the active ingredient, e.g., it retains at least about 85% of un-degraded active, in some embodiments, at least about 90%, and in some embodiments, at least about 95%, after storage at 2-30° C. for a 2-3 year period of time.

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF can also be used.

The term "pharmaceutical composition" as used herein shall mean a composition that is made under conditions such that it is suitable for administration to humans, e.g., it is made under good manufacturing practice (GMP) conditions and contains pharmaceutically acceptable excipients, e.g., without limitation, stabilizers, bulking agents, buffers, carriers, diluents, vehicles, solubilizers, and binders. As used herein "pharmaceutical composition" includes, but is not limited to, a pre-drying solution(s) or dispersion(s) as well as a liquid form ready for injection or infusion after reconstitution of a dry-powder preparation.

A "pharmaceutical dosage form" as used herein means the pharmaceutical compositions disclosed herein being in a form of a capsule (usually referred to as single oral solid dosage form) or in a container and in an amount suitable for reconstitution and administration of one or more doses, typically about 1-2, 1-3, 1-4, 1-5, 1-6, 1-10, or about 1-20 doses. The ultimate dosage form can be sterile, fluid and stable under the conditions of manufacture and storage. The prevention of the growth of microorganisms can be accomplished by various antibacterial and antifungal agents, for example, parabens, chlorobutanol, phenol, sorbic acid, thimerosal, and the like.

The single or multiple dosages which can be used include an amount of Compound 1 independently selected from about 0.1 mg/kg to about 600 mg/kg body weight, or about 1.0 mg/kg to about 500 mg/kg body weight, or about 1.0 mg/kg to about 400 mg/kg body weight, or about 1.0 mg/kg to about 300 mg/kg body weight, or about 1.0 mg/kg to about 200 mg/kg body weight, or about 1.0 mg/kg to about 100 mg/kg body weight, or about 1.0 mg/kg to about 50 mg/kg body weight, or about 1.0 mg/kg to about 30 mg/kg body weight, or about 1.0 mg/kg to about 10 mg/kg body weight, or about 10 mg/kg to about 600 mg/kg body weight, or about 10 mg/kg to about 500 mg/kg body weight, or about 10 mg/kg to about 400 mg/kg body weight, or about 10 mg/kg to about 300 mg/kg body weight, or about 10 mg/kg to about 200 mg/kg body weight, or about 10 mg/kg to about 100 mg/kg body weight, or about 50 mg/kg to about 150 mg/kg body weight, or about 100 mg/kg to about 200 mg/kg body weight, or about 150 mg/kg to about 250 mg/kg body weight, or about 200 mg/kg to about 300 mg/kg body weight, or about 250 mg/kg to about 350 mg/kg body weight, or about 200 mg/kg to about 400 mg/kg body weight, or about 300 mg/kg to about 400 mg/kg body weight, or about 250 mg/kg to about 300 mg/kg body weight, or about 300 mg/kg body weight. In some embodiments, the amount of Compound 1 is about 90 mg, about 100 mg, about 110 mg, or about 120 mg per dose. In some embodiments, the amount of Compound 1 is about 100 mg per dose. In some embodiments, the maximum clinical dose is 1000 mg/day. Compounds of the present disclosure may be administered in a single daily dose, or the total daily dosage may be administered in divided dosage of two, three or four times daily.

Single or multiple doses can be administered. In some embodiments, the dose is administered once, twice, three times, four times, five times, or six times. In some embodiments, the dose is administered once per day, twice per day, three times per day, or four times per day. In some embodiments, the dose is administered every hour, every two hours, every three hours, every four hours, every 6 hours, every 12 hours, or every 24 hours.

Also provided are articles of manufacture and kits comprising a pharmaceutical composition which comprises Compound 1 and/or the hydroquinone form thereof, for use in any of the methods described herein.

As used herein, the term "excipient" means the substances used to formulate active pharmaceutical ingredients (API) into pharmaceutical formulations; in an embodiment, an excipient does not lower or interfere with the primary therapeutic effect of the API. In some embodiments, an excipient is therapeutically inert. The term "excipient" encompasses carriers, diluents, vehicles, solubilizers, stabilizers, bulking agents, and binders. Excipients can also be those substances present in a pharmaceutical formulation as an indirect or unintended result of the manufacturing process. In some embodiments, excipients are approved for or considered to be safe for human and animal administration, e.g., generally regarded as safe (GRAS) substances. GRAS substances are listed by the Food and Drug administration in the Code of Federal Regulations (C.F.R.) at 21 C.F.R. § 182 and 21 C.F.R. § 184, incorporated herein by reference. In some embodiments, excipients include, but are not limited to, hexitols, including mannitol and the like.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is a human.

As used herein, the terms "therapeutic agent" and "therapeutic agents" refer to any agent(s) which can be used in the treatment or prevention of a disease or one or more symptoms thereof. In certain embodiments, the term "therapeutic agent" includes a compound as described herein. In certain embodiments, a therapeutic agent is an agent which is known to be useful for, or has been or is currently being used for the treatment or prevention of a disease or one or more symptoms thereof.

"Therapeutic use" of the compounds discussed herein is defined as using one or more of the compounds discussed herein to treat or suppress a disorder, as defined herein. A As used herein "therapeutically effective amount" of a compound is an amount of the compound, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations.

As used herein "Treating" or "treatment of" a disorder with the pharmaceutical compositions and methods discussed herein is defined as administering a pharmaceutical composition discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the pharmaceutical compositions and methods discussed herein is defined as administering a pharmaceutical composition discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. In some embodiments, genetic screening can be used to identify patients at risk of the disorder. The pharmaceutical compositions and methods disclosed herein can then be administered to asymptomatic patients at risk of developing the clinical symptoms of the disorder, in order to suppress the appearance of any adverse symptoms.

In certain embodiments, the pharmaceutical composition is stable when stored at about 15° C. to about 25° C. and about 60% relative humidity for a duration of time of at least one month, at least two months, at least 3 months, or at least six months. In certain embodiments, the pharmaceutical composition is stable when stored at about 25° C. and about 60% relative humidity for a duration of time of at least one month, at least two months, or at least 3 months. In certain embodiments, the pharmaceutical composition is stable when stored at about 40° C. and about 75% relative humidity for a duration of time of at least one month, at least two months, at least three months, or at least six months. In certain embodiments, the pharmaceutical composition is stable when stored at about 40° C. and about 75% relative humidity for a duration of time of at least one month, at least two months, or at least three months.

In certain embodiments, the pharmaceutical composition is an oral pharmaceutical composition. In certain embodiments, the pharmaceutical composition is a transdermal pharmaceutical composition.

In certain embodiments, the pharmaceutical composition is an oral pharmaceutical composition and has bioavailability when administered with a low-fat food which differs from bioavailability when administered with a medium-fat food by a percentage difference of about 90% or less, about 85% or less, about 80% or less, about 75% or less, about 70% or less, or about 65% or less.

In certain embodiments, the oral pharmaceutical composition bioavailability for Medium-fat Food for Testing is about 45 to about 55%, in some embodiments, or about 40% to about 50% in some embodiments, for a pharmaceutical formulation made from a vehicle which comprises a): about 60 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 20 wt/wt % polysorbate 80 (e.g. Tween 80); wherein the % weight of the components in a) total 100%. In certain embodiments, the oral pharmaceutical composition bioavailability for Medium-fat Food for Testing is about 49% to about 50%, in some embodiments, for a pharmaceutical formulation made from a vehicle which comprises in a): about 60 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 20 wt/wt % polysorbate 80 (e.g. Tween 80); wherein the % weight of the components in a) total 100%. In certain embodiments, the oral pharmaceutical composition bioavailability for Low-fat Food for Testing is about 10 to about 15%, in some embodiments, for a pharmaceutical formulation made from a vehicle which comprises in a): about 60 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 20 wt/wt % polysorbate 80 (e.g. Tween 80); wherein the % weight of the components in a) total 100%. In certain embodiments, the oral pharmaceutical composition bioavailability for Low-fat Food for Testing is about 13%, in some embodiments, for a pharmaceutical formulation made from a vehicle which comprises in a): about 60 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 20 wt/wt % polysorbate 80 (e.g. Tween 80); wherein the % weight of the components in a) total 100%.

In certain embodiments, the oral pharmaceutical composition bioavailability for Medium-fat Food for Testing is about 15% to about 40%, in some embodiments, about 25% to about 35%, in some embodiments, for a pharmaceutical formulation made from a vehicle which comprises in a): about 65 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 15 wt/wt % polysorbate 80 (e.g. Tween 80); wherein the % weight of the components in a) total 100%. In certain embodiments, the oral pharmaceutical composition bioavailability for Medium-fat Food for Testing is about 29% for a pharmaceutical formulation made from a vehicle which comprises in a): about 65 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 15 wt/wt % polysorbate 80 (e.g. Tween 80); wherein the % weight of the components in a) total 100%. In certain embodiments, the oral pharmaceutical composition bioavailability for Low-fat Food for Testing is about 10% to about 15% for a pharmaceutical formulation made from a vehicle which comprises in a): about 65 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 15 wt/wt % polysorbate 80 (e.g. Tween 80); wherein the % weight of the components in a) total 100%. In certain embodiments, the oral pharmaceutical composition bioavailability for Medium-fat Food for Testing is about 14% for a pharmaceutical formulation made from a vehicle which comprises in a): about 65 wt/wt % a pharmaceutically acceptable oil (e.g. Labrafac WL 1349, sesame oil, cottonseed oil, soybean oil, Labrafac PG, olive oil, or corn oil), about 20 wt/wt % propylene glycol laurates composition (e.g. Lauroglycol 90), and about 15 wt/wt % polysorbate 80 (e.g. Tween 80); wherein the % weight of the components in a) total 100%.

In certain embodiments, the pharmaceutical composition shows no birefringent crystals when stored at about 15° C. to about 25° C. and about 60% relative humidity or at about 40° C. and about 75% relative humidity for a duration of time of at least about one month. In certain embodiments, the pharmaceutical composition shows no birefringent crystals when stored at about 25° C. and about 60% relative humidity or at about 40° C. and about 75% relative humidity for a duration of time of at least about one month. In certain embodiments, the pharmaceutical composition showed no birefringent when stored at about 15° C. to about 25° C. and about 60% relative humidity for a duration of time of at least about one month. In certain embodiments, the pharmaceutical composition showed no birefringent when stored at about 25° C. and about 60% relative humidity for a duration of time of at least about one month. In certain embodiments, the pharmaceutical composition showed no birefringent when stored at about 40° C. and about 75% relative humidity for a duration of time of at least about one month, at least three months, or at least six months. In certain embodiments, the pharmaceutical composition showed no birefringent when stored at about 40° C. and about 75% relative humidity for a duration of time of at least about one month.

In certain embodiments, the pharmaceutical composition's total impurity level increases by 25% or less from an initial total impurity level to a subsequent total impurity level. In some embodiments, the pharmaceutical composition is stored at about 40° C. and about 75% relative humidity for at least about one month, at least about two months, or at least about three months. In certain embodiments, optionally the initial total impurity level is measured on the day the pharmaceutical composition is prepared and before it is stored (on the same day as it is prepared) at 40° C. and about 75% relative humidity. In some or any embodiments, the subsequent total impurity level is tested after about one month, about two months, or about 3 months in storage. In certain embodiments, the initial total impurity level is about 2% or less, about 1% or less, about 0.5% or less, about 0.4% or less, or about 0.3% or less. In some embodiments, the pharmaceutical composition's total impurity level increases from an initial total impurity level to a subsequent impurity level by 25% or less, 20% or less, 15% or less.

In certain embodiments, the vehicle a) in the pharmaceutical composition comprises about 60% w/w pharmaceutically acceptable oil (for example, a Labrafac-like oil (Labrafac WL 1349 or Labrafac PG), sesame oil, cottonseed oil, soybean oil, olive oil, or corn oil); about 20 w/w % propylene glycol laurates composition (Lauroglycol 90); and about 20 w/w % polysorbate 80 (Tween 80); wherein the % weight of the components in a) total 100%. In certain embodiments, the vehicle a) in the pharmaceutical composition comprises about 65% w/w pharmaceutically acceptable oil (for example, a Labrafac-like oil (Labrafac WL 1349 or Labrafac PG), sesame oil, cottonseed oil, soybean oil, olive oil, or corn oil); about 20 w/w % propylene glycol laurates composition (Lauroglycol 90); and about 15 w/w % polysorbate 80 (Tween 80); wherein the % weight of the components in a) total 100%.

In certain embodiments, the pharmaceutical composition comprises about 100 to about 120 mg of Compound 1, per g of a)+b)+c). In certain embodiments, the pharmaceutical composition comprises about 100 mg of Compound 1, tog of a). In certain embodiments, the pharmaceutical composition comprises about 120 mg of Compound 1, to g of a)+b)+c).

In certain embodiments, Compound 1 is provided in a capsule and the weight of Compound 1 in the capsule is selected from the group consisting of about 50 mg and about 60 mg. In certain embodiments, Compound 1 is provided in a capsule and the weight of Compound 1 in the capsule is about 50 mg. In certain embodiments, the weight of Compound 1 in the capsule is about 60 mg.

In certain embodiments, the pharmaceutical composition shows about 2% or less change in potency from an initial potency after storing at about 15° C. to about 25° C. and about 60% relative humidity or at about 40° C. and about 75% relative humidity for a duration of time of at least one month. In certain embodiments, the pharmaceutical composition shows about 2% or less change in potency from an initial potency after storing at about 25° C. and about 60% relative humidity or at about 40° C. and about 75% relative humidity for a duration of time of at least one month. In certain embodiments, the pharmaceutical composition shows about 2% or less change in potency from an initial potency after storing at about 15° C. to about 25° C. and about 60% relative humidity for a duration of time of at least one month. In certain embodiments, the pharmaceutical composition shows about 2% or less change in potency from an initial potency after storing at about 25° C. and about 60% relative humidity for a duration of time of at least one month. In certain embodiments, the pharmaceutical composition shows about 2% or less change in potency from an initial potency after storing stored at about 40° C. and about 75% relative humidity for a duration of time of at least one month. In certain embodiments, optionally the initial potency is measured on the day the pharmaceutical composition is prepared and before it is stored on the same day as it is prepared.

In certain embodiments, the pharmaceutical composition shows about 1% or less degradation from an initial degradation level after storing at about 15° C. to about 25° C. and about 60% relative humidity or at about 40° C. and about 75% relative humidity for a duration of time of at least one month. In certain embodiments, the pharmaceutical composition shows about 1% or less degradation from an initial degradation level after storing at about 25° C. and about 60% relative humidity or at about 40° C. and about 75% relative humidity for a duration of time of at least one month. In certain embodiments, the pharmaceutical composition shows about 1% or less degradation from an initial degradation level after storing at about 15° C. to about 25° C. and about 60% relative humidity for a duration of time of at least one month. In certain embodiments, the pharmaceutical composition shows about 1% or less degradation from an initial degradation level after storing at about 25° C. and about 60% relative humidity for a duration of time of at least one month. In certain embodiments, the pharmaceutical composition shows about 1% or less degradation from an initial degradation level after storing at about 40° C. and about 75% relative humidity for a duration of time of at least one month. In certain embodiments, optionally the initial degradation level is measured on the day the pharmaceutical composition is prepared and before it is stored on the same day as it is prepared.

In certain embodiments, the pharmaceutical composition is in a capsule. In certain embodiments, the pharmaceutical composition is a hard gelatin capsule. In certain embodiments, any water content in the gelatin of the hard gelatin capsule is about 20% or less, about 10% to about 20%, or about 11% to about 16%, when stored for about one month, about one or more months, about three months, or about three or more months.

In certain embodiments, the oral pharmaceutical composition is a solution. In certain embodiments, the oral pharmaceutical composition comprises about 50 mg to about 120 mg of Compound 1 per g of a)+b)+c). In certain embodiments, the oral pharmaceutical composition's strength is selected from the group consisting of about 60 mg/mL and about 100 mg/mL of Compound 1.

In certain embodiments, the oral pharmaceutical composition is stable when stored at about 25° C. and about 60% relative humidity or at about 40° C. and about 75% relative humidity for a duration of time of at least about one month, at least about three months, or at least about six months. In certain embodiments, the oral pharmaceutical composition is stable when stored at about 5° C. for a period of at least about 4 weeks. In certain embodiments, stability studies are performed following ICH stability guidelines.

In certain embodiments, the oral pharmaceutical composition comprises an optional flavorant. In certain embodiments, the amount of the optional flavorant is about 0 to about 2% wt/wt %. In certain embodiments, the amount of the optional flavorant is about 0 to about 1 wt/wt %. In certain embodiments, the optional flavorant is less than 1% wt/wt %. In certain embodiments, the flavorant is an oil-soluble flavorant.

In certain embodiments, the flavorant is selected from the group consisting of natural flavors, natural fruit flavors, artificial flavors, artificial fruit flavors, flavor enhancers and mixtures thereof. In certain embodiments, the flavorant is selected from one or more of natural flavors. In certain embodiments, the flavorant is selected from one or more of natural fruit flavors. In certain embodiments, the flavorant is selected from one or more of artificial flavors. In certain embodiments, the flavorant is selected from one or more of artificial fruit flavors. In certain embodiments, the flavorant is selected from one or more of flavor enhancers.

In certain embodiments, the flavorant has a flavor selected from the group consisting of raspberries, punch, cherry, strawberries, and blueberries. In certain embodiments, the flavorant has the flavor of raspberries. In certain embodiments, the flavorant has the flavor of punch. In certain embodiments, the flavorant has the flavor of cherry. In certain embodiments, the flavorant has the flavor of strawberries. In certain embodiments, the flavorant has the flavor of blueberries.

In certain embodiments, the flavorant has an odor selected from the group consisting of raspberries, punch, cherry, strawberries, and blueberries. In certain embodiments, the flavorant has the odor of raspberries. In certain embodiments, the flavorant has the odor of punch. In certain embodiments, the flavorant has the odor of cherry. In certain embodiments, the flavorant has the odor of strawberries. In certain embodiments, the flavorant has the odor of blueberries.

In certain embodiments, the pharmaceutically acceptable oil is selected from one or more (in some embodiments, 1, 2, or 3; in some embodiments, 1 or 2; in some embodiments, 1) of the group consisting of: a Labrafac-like oil (including Labrafac WL 1349 and Labrafac PG), sesame oil, cottonseed oil, soybean oil, olive oil, and corn oil. In some embodiments, the pharmaceutically acceptable oil is selected from one or more (in some embodiments, 1, 2, or 3; in some embodiments, 1 or 2; in some embodiments, 1) of the group consisting of: a Labrafac-like oil (including Labrafac WL 1349 and Labrafac PG), cottonseed oil, soybean oil, olive oil, and corn oil. In some embodiments, the pharmaceutically acceptable oil is selected from one or more (in some embodiments, 1, 2, or 3; in some embodiments, 1 or 2; in some embodiments, 1) of the group consisting of: a Labrafac-like oil (including Labrafac WL 1349 and Labrafac PG), sesame oil, cottonseed oil, soybean oil, and corn oil. In some embodiments, the pharmaceutically acceptable oil is selected from one or more (in some embodiments, 1, 2, or 3; in some embodiments, 1 or 2; in some embodiments, 1) of the group consisting of: a Labrafac-like oil (including Labrafac WL 1349 and Labrafac PG), cottonseed oil, soybean oil, and corn oil.

In some or any embodiments, the pharmaceutically acceptable oil is not a Gelucire-like oil.

In some or any embodiments of the sixth aspect, the Gelucire-like oil is Gelucire 44/14. In some or any embodiments of the sixth aspect, the ratio of the Gelucire-like oil to a surfactant (e.g. TPGS) to the polysorbate 80 is about 80:10:10.

In certain embodiments, the pharmaceutical composition comprises b)

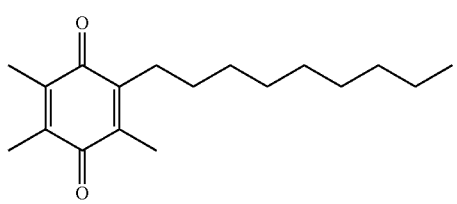

Compound 1 or one or more members selected from the group consisting of hydrates and solvates thereof.

In certain embodiments, the pharmaceutical composition comprises b)

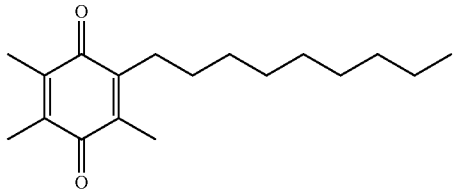

Compound 1

(not as a hydrate of solvate thereof).

In certain embodiments, the pharmaceutical composition comprises b), the hydroquinone form of

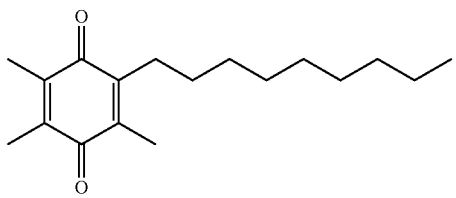

Compound 1 or one or more members selected from the group consisting of hydrates and solvates thereof.

In certain embodiments, the pharmaceutical composition comprises b), the hydroquinone form of

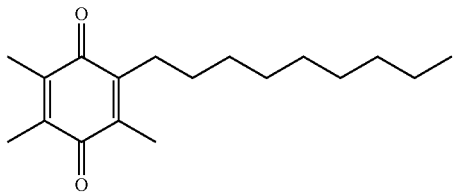

Compound 1

(not as a hydrate or solvate thereof).

Description of the polymorph, which can be used herein to prepare the pharmaceutical compositions disclosed herein, are provided in PCT Application Publication No. WO 2020/081879, which is hereby incorporated by reference in its entirety.

Particle size distribution can be determined by laser diffraction, using a Malvern 3000 Mastersizer. Settings are shown in Table A.

TABLE A

| Malvern Instrument Settings | |
|---|---|
| Particle Type | |
| Non-spherical particle mode | Yes |
| Is Fraunhofer type | No |
| Material Properties | |
| Refractive index | 1.480 |
| Absorption index | 0.001 |
| Particle density | 1.00 g/cm$^3$ |
| Different optical properties in blue light | Yes |
| Refractive index (in blue light) | 1.480 |
| Absorption index (in blue light) | 0.001 |
| Dispersant properties | |
| Dispersant name | Water |
| Refractive index | 1.330 |
| Level sensor threshold | 100.000 |
| Measurement Duration | |
| Background measurement duration (red) | 15.00 s |
| Sample measurement duration (red) | 15.00 s |
| Perform blue light measurement? | Yes |
| Background measurement duration (blue) | 15.00 s |
| Sample measurement duration (blue) | 15.00 s |
| Assess light background stability | No |
| Measurement sequence | |
| Aliquots | 1 |
| Automatic number of measurements | No |
| Pre-alignment delay | 0.00 s |
| Number of measurements | 3 |
| Delay between measurements | 0.00 s |
| Pre-measurement delay | 0.00 s |
| Close measurement window after measurement | No |
| Measurement obscuration settings | |
| Auto start measurement | No |
| Obscuration low limit | 1.00% |
| Obscuration high limit | 10.00% |
| Enable obscuration filtering | No |
| Measurement alarms | |
| Use Background Check | No |
| Background Check Limits | [1, 200], [20, 60] |

Particles are generally polydisperse, i.e., not all the same size. One measure of polydispersity is the ratio D90/D10. D10 represents the particle diameter corresponding to 10% cumulative (from 0 to 100%) undersize particle size distribution (i.e. the percentage of particles smaller than D10 is 10%). D90 represents the particle diameter corresponding to 90% cumulative (from 0 to 100%) undersize particle size distribution (i.e. the percentage of particles smaller than D90 is 90%). D90 and D10 are determined by laser diffraction, discussed above, unless expressly stated otherwise.

In some embodiments, the polymorph, which can be used herein to prepare the pharmaceutical compositions disclosed herein, is according to any one of Embodiments 1-10.

Embodiment 1A. In certain embodiments, provided is a method, according to the second aspect in the Summary, of preparing a pharmaceutical composition described herein, comprising adding about 1 wt/wt % to about 12 wt/wt %, about 4 wt/wt % to about 12 wt/wt %, about 5 wt/wt % to about 10 wt/wt %, 5 wt/wt %, about 6 wt/wt %, about 7 wt/wt %, about 8 wt/wt %, about 9 wt/wt %, or about 10 wt/wt % Compound 1 and/or the hydroquinone form thereof per g of a)+b)+c), wherein Compound 1 and/or the hydroquinone form thereof is optionally a hydrate thereof, and/or solvate thereof; to the mixture from step a)+b)+c).

Embodiment 1B. In certain embodiments, provided is a method, according to the second aspect in the Summary, of preparing a pharmaceutical composition described herein, comprising adding about 1 wt/wt % to about 12 wt/wt %, about 4 wt/wt % to about 12 wt/wt %, about 5 wt/wt % to about 10 wt/wt %, 5 wt/wt %, about 6 wt/wt %, about 7 wt/wt %, about 8 wt/wt %, about 9 wt/wt %, or about 10 wt/wt % Compound 1 and/or the hydroquinone form thereof per g of a)+b)+c), wherein Compound 1 and/or the hydroquinone form thereof is optionally a hydrate thereof, and/or solvate thereof; to the mixture from step a)+b)+c). In certain embodiments, provided is a method, according to the second aspect in the Summary, of preparing a pharmaceutical composition described herein, wherein step b) occurs at room temperature.

Embodiment 2. In embodiments of the first aspect in the Summary, the second aspect in the Summary, and Embodiments 1A and 1B, Compound 1 is a polymorph of an anhydrate of 2,3,5-trimethyl-6-nonylcyclohexa-2,5-diene-1,4-dione, wherein a powder X-ray diffraction pattern for the polymorph comprises characteristic peaks at least at the following angular positions, wherein the angular positions may vary by ±0.2: 4.10, 12.12, and 16.14, and wherein the characteristic peaks are measured using a Cu Kα1 source, and a wavelength of 1.540598 Å. In some embodiments, the characteristic peaks are measured at room temperature, in some embodiments at a temperature of 23-25° C. In some embodiments, Compound 1 in step b) is a polymorph of an anhydrate of 2,3,5-trimethyl-6-nonylcyclohexa-2,5-diene-1,4-dione, wherein a powder X-ray diffraction pattern for the polymorph comprises characteristic peaks at least at the following angular positions, wherein the angular positions may vary by ±0.2: 4.10, 12.12, and 16.14, and wherein the characteristic peaks are measured using a Cu Kα1 source, and a wavelength of 1.540598 Å. In some embodiments, the characteristic peaks are measured at room temperature, in some embodiments at a temperature of 23-25° C.

Embodiment 2A. The polymorph of Embodiment 2, comprising characteristic peaks at least at the following angular positions, wherein the angular positions may vary by ±0.2: 4.10, 11.77, 12.12, and 16.14.

Embodiment 3. The polymorph of Embodiment 2, comprising characteristic peaks at least at the following angular positions, wherein the angular positions may vary by ±0.2: 4.10, 11.77, 12.12, 16.14, and 22.41.

Embodiment 4. The polymorph of any one of Embodiments 2-3, wherein the angular positions may vary by ±0.1.

Embodiment 5. The polymorph of any one of Embodiments 2-3, wherein the angular positions may vary by ±0.05.

Embodiment 6. The polymorph of any one of Embodiments 2-5, wherein the polymorph has a powder x-ray diffraction pattern substantially as shown in any one of FIGS. 5, 11, 14, and 16 as provided in WO 2020/081879.

Embodiment 7. The polymorph of any one of Embodiments 2-6, having a differential scanning calorimetry (DSC) thermogram substantially as shown in FIG. 7 as provided in WO 2020/081879.

Embodiment 8. The polymorph of any one of Embodiments 2-7, wherein a DSC thermogram has a single endothermic peak at about 47 to about 53° C.

Embodiment 9. The polymorph of any one of Embodiments 2-8, having a thermogravimetric analysis (TGA) thermogram substantially as shown in FIG. 8 as provided in WO 2020/081879.

Embodiment 10. The polymorph of any one of Embodiments 2-9, having a $^1$H NMR spectrum substantially as shown in FIG. 6 as provided in WO 2020/081879.

Embodiment 11. A composition comprising the polymorph of any one of Embodiments 2-10, wherein at least about 95% by mole of the 2,3,5-trimethyl-6-nonylcyclohexa-2,5-diene-1,4-dione is the polymorph, exclusive of any solvents, carriers or excipients.

Embodiment 12. A composition comprising the polymorph of any one of Embodiments 2-10, wherein at least about 99% by mole of the 2,3,5-trimethyl-6-nonylcyclohexa-2,5-diene-1,4-dione is the polymorph, exclusive of any solvents, carriers or excipients.

Embodiment 13. A composition comprising the polymorph of any one of Embodiments 2-10, or the composition of Embodiment 11 or 12, wherein at least about 95% a/a as measured by HPLC of the composition is the 2,3,5-trimethyl-6-nonylcyclohexa-2,5-diene -1,4-dione, exclusive of any solvents, carriers or excipients.

Embodiment 14. A composition comprising the polymorph of any one of Embodiments 2-10, or the composition of Embodiment 11 or 12, wherein at least about 99% a/a as measured by HPLC of the composition is the 2,3,5-trimethyl-6-nonylcyclohexa-2,5-diene -1,4-dione, exclusive of any solvents, carriers or excipients.

Embodiment 15. A composition comprising the polymorph of any one of Embodiments 2-10, or the composition of any one of Embodiments 11-14, wherein the potency of the 2,3,5-trimethyl-6-nonylcyclohexa-2,5-diene-1,4-dione is at least about 95%.

Embodiment 16. A composition comprising the polymorph of any one of Embodiments 2-10, or the composition of any one of Embodiments 11-14, wherein the potency of the 2,3,5-trimethyl-6-nonylcyclohexa-2,5-diene-1,4-dione is at least about 99%.

Embodiment 17. A composition comprising the polymorph of any one of Embodiments 2-10, or the composition of any one of Embodiments 11-16, wherein the polymorph is present as a plurality of particles, wherein the particles have a ratio of D90:D10 less than about 11:1.

Embodiment 18. A composition comprising the polymorph of any one of Embodiments 2-10, or the composition of any one of Embodiments 11-16, wherein the polymorph is present as a plurality of particles, wherein the particles have a ratio of D90:D10 less than about 7:1.

Embodiment 19. A composition comprising the polymorph of any one of Embodiments 2-10, or the composition of any one of Embodiments 11-18, wherein the polymorph was recrystallized by a solvent comprising about 75-85% IPA/water.

Embodiment 20. A composition comprising the polymorph of any one of Embodiments 2-10, or the composition of any one of Embodiments 11-19, wherein the polymorph was recrystallized by a solvent comprising about 80-85% IPA/water.

Embodiment 21. A composition comprising the polymorph of any one of Embodiments 2-10, or the composition of any one of Embodiments 11-19, wherein the polymorph was recrystallized by a solvent comprising about 85% IPA/water.

Additional Embodiments

Embodiment 21A. Provided herein is a pharmaceutical composition comprising:
a) 55-75 wt/wt % of Labrafac, 15-25 wt/wt % of Lauroglycol 90, and 10-20 wt/wt % of Tween 80, wherein the wt/wt % of Labrafac, Lauroglycol 90, and Tween 80 total 100%; and b) about 90 to about 120 mg of Compound 1:

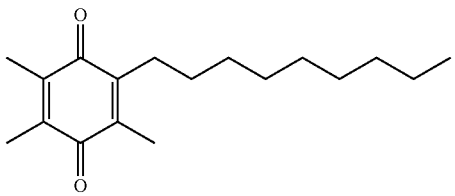 [SMILES: CCCCCCCCCC1=C(C)C(=O)C(C)=C(C)C1=O]

and/or the hydroquinone form thereof per g of a); wherein the Compound 1, and/or the hydroquinone thereof is optionally a hydrate thereof, and/or solvate thereof; and wherein when Compound 1, and/or hydroquinone thereof, is in the form of a hydrate and/or solvate, then the about 90 to about 120 mg weight of Compound 1, and/or its hydroquinone does not include the weight of the water in the hydrate or the weight of the solvent in the solvate.

Embodiment 22. The pharmaceutical composition of embodiment 21A, wherein the pharmaceutical composition is stable when stored at about 25° C. and about 60% relative humidity or at about 40° C. and about 75% relative humidity for a duration of time of at least about one month.

Embodiment 23. The pharmaceutical composition of any one of embodiments 21A-22, wherein the pharmaceutical composition shows no birefringent crystals when stored at about 25° C. and about 60% relative humidity or at about 40° C. and about 75% relative humidity for a duration of time of at least about one month.

Embodiment 24. The pharmaceutical composition of any one of embodiments 21A-23, wherein the pharmaceutical composition shows no birefringent crystals when stored at about 25° C. and about 60% relative humidity for a duration of at least about one month.

Embodiment 25. The pharmaceutical composition of any one of embodiments 21A-23, wherein the pharmaceutical composition shows no birefringent crystals when stored at about 40° C. and about 75% relative humidity for a duration of at least about one month.

Embodiment 26. The pharmaceutical composition of any one of embodiments 21A-25, wherein the total impurity level increases by 25% or less from an initial total impurity level to a subsequent total impurity level, when stored at about 40° C. and about 75% relative humidity for at least about three months, optionally wherein the initial total impurity level is measured on the day the pharmaceutical composition is prepared and before it is stored, on the same day as it is prepared, at 40° C. and about 75% relative humidity; and wherein the subsequent total impurity level is tested after about 3 months in storage.

Embodiment 27. The pharmaceutical composition of embodiment 26, wherein the subsequent total impurity level is about 1% or less, about 0.5% or less, or about 0.4% or less.

Embodiment 28. The pharmaceutical composition of any one of embodiments 21A-27, wherein a) comprises about 60% w/w Labrafac; about 20% w/w Lauroglycol 90; and about 20% w/w Tween 80.

Embodiment 29. The pharmaceutical composition of any one of embodiments 21A-27, wherein a) comprises about 65% w/w Labrafac; about 20% w/w Lauroglycol 90; and about 15% w/w Tween 80.

Embodiment 30. The pharmaceutical composition of any one of embodiments 21A-29, wherein the pharmaceutical composition comprises about 100 mg of Compound 1 to g of a).

Embodiment 31. The pharmaceutical composition of any one of embodiments 21A-30, wherein the total weight of the pharmaceutical composition is selected from the group consisting of about 50 mg to about 60 mg.

Embodiment 32. The pharmaceutical composition of any one of embodiments 21A-31, wherein the total weight of the pharmaceutical composition is about 50 mg.

Embodiment 33. The pharmaceutical composition of any one of embodiments 21A-31, wherein the pharmaceutical composition is about 60 mg.

Embodiment 34. The pharmaceutical composition of embodiment 21A-32 or 21A-33, wherein the pharmaceutical composition shows about 2% or less change in potency from an initial potency after storing at about 25° C. and about 60% relative humidity or at about 40° C. and about 75% relative humidity for a duration of time of at least one month; optionally wherein the initial potency is measured on the day the pharmaceutical composition is prepared and before it is stored on the same day as it is prepared.

Embodiment 35. The pharmaceutical composition of embodiment 21A-32 or 21A-33, wherein the pharmaceutical composition shows about 1% or less degradation from an initial degradation level after storing at about 25° C. and about 60% relative humidity or at about 40° C. and about 75% relative humidity for a duration of time of at least one month; optionally wherein the initial degradation level is measured on the day the pharmaceutical composition is prepared and before it is stored on the same day as it is prepared.

Embodiment 36. The pharmaceutical composition of any one of embodiments 1-35, wherein b) is

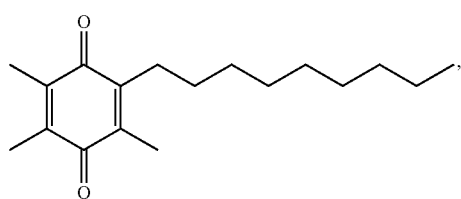

Compound 1 or one or more members selected from the group consisting of hydrates thereof and solvates thereof.

Embodiment 37. The pharmaceutical composition of any one of embodiments 1-36, wherein b) is

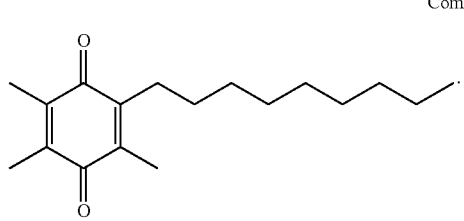

Compound 1

Embodiment 38. The pharmaceutical composition of any one of embodiments 1-35, wherein b) is the hydroquinone form of

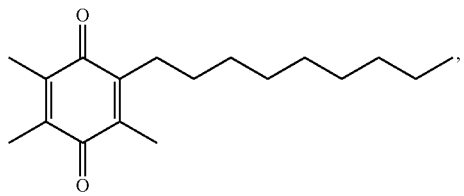

Compound 1 or one or more members selected from the group consisting of hydrates thereof, and solvates thereof.

Embodiment 39. The pharmaceutical composition of any one of embodiments 1-35 and 38, wherein b) is the hydroquinone form of

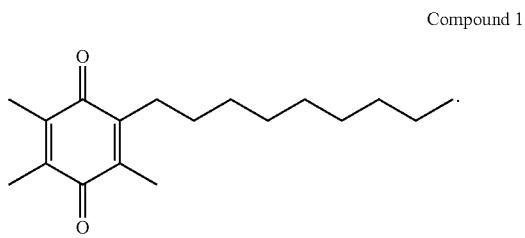 [SMILES: CCCCCCCCCC1=C(C)C(=O)C(C)=C(C)C1=O]

Compound 1

Embodiment 40. The pharmaceutical composition of any one of embodiments 21A-39, wherein the pharmaceutical composition is an oral pharmaceutical composition.

Embodiment 41. The pharmaceutical composition of embodiment 40, wherein the oral pharmaceutical composition is in a capsule.

Embodiment 42. The pharmaceutical composition of embodiment 41, wherein the capsule is a hard gelatin capsule.

Embodiment 43. The pharmaceutical composition of embodiment 42, wherein any water content in the gelatin of the hard gelatin capsule is about 20% or less, about 10% to about 20%, or about 11% to about 16%, when stored for about one month, about one or more months, about three months, or about three or more months.

Embodiment 44. The pharmaceutical composition of any one of embodiments 40-43, wherein the pharmaceutical composition has bioavailability when administered with a low-fat food which differs from bioavailability when administered with a medium-fat food by a percentage difference of about 90% or less, about 85% or less, about 80% or less, about 75% or less, about 70% or less, or about 65% or less.

Embodiment 45. The pharmaceutical composition of any one of embodiments 40-43, wherein oral bioavailability for medium-fat food is about 40 to about 50%, in some embodiments, about 49%.

Embodiment 46. The pharmaceutical composition of embodiments 40-43 and 45, wherein oral bioavailability for low-fat food is about 10% to about 15%, in some embodiments, about 13%.

Embodiment 47. The pharmaceutical composition of any one of embodiments 20-23, wherein oral bioavailability for medium-fat food is about 25% to about 35%, in some embodiments, about 29%.

Embodiment 48. The pharmaceutical composition of embodiments 40-43 and 47, wherein oral bioavailability for low-fat food is about 10% to about 15%, in some embodiments, about 14%.

Embodiment 49. The pharmaceutical composition of any one of embodiments 21A-48, wherein the oral pharmaceutical composition comprises about 100 mg to about 120 mg of Compound 1 per g of a).

Embodiment 50. The pharmaceutical composition of any one of embodiments 21A-42, wherein the pharmaceutical composition is a transdermal pharmaceutical composition.

Embodiment 51. A method of preparing a pharmaceutical composition of any one of embodiments 21A-50, comprising:
 step a) mixing 55-75 wt/wt % of Labrafac, 15-25 wt/wt % of Lauroglycol 90, and 10-20 wt/wt % of Tween 80, wherein the wt/wt % of Labrafac, Lauroglycol 90, and Tween 80 total 100%;
 step b) adding about 90 mg to about 120 mg of Compound 1 and/or the hydroquinone form thereof per g of a), wherein Compound 1 and/or the hydroquinone form thereof is optionally a hydrate and/or solvate thereof; to the mixture from step a) and mixing;
 and wherein when the Compound 1, and/or hydroquinone thereof, is in the form of a hydrate and/or solvate, then the about 90 to about 120 mg weight of Compound 1 and/or its hydroquinone, does not include the weight of any the water in the hydrate or the weight of the solvent in the solvate.

Embodiment 52. The method of embodiment 51, wherein step b) occurs at room temperature.

Embodiment 53. The method of embodiment 51 or 52, wherein Compound 1 in step b) is a polymorph of an anhydrate of 2,3,5-trimethyl-6-nonylcyclohexa-2,5-diene-1,4-dione, wherein a powder X-ray diffraction pattern for the polymorph comprises characteristic peaks at least at the following angular positions, wherein the angular positions may vary by ±0.2: 4.10, 12.12, and 16.14, and wherein data are obtained with a Cu Kα1 source, a wavelength of 1.540598 Å, and at a temperature of 23-25° C.

Embodiment 54. The method of any one of embodiments 51-53, wherein Compound 1 is added and mixed under light protection or yellow light.

Embodiment 55. A pharmaceutical composition prepared by the method of any one of embodiments 51-54.

Embodiment 56. A method for treating or suppressing a disease or disorder selected from the group consisting of an α-synucleinpathy, a tauopathy, an autistic spectrum disorder, a pervasive developmental disorder, a liver disease, liver damage, dementia, and reperfusion injury, comprising administering a pharmaceutical composition of any one of embodiments 1-49 or a pharmaceutical composition of embodiment 55.

Embodiment 57. The method of embodiment 56, wherein the α-synucleinpathy is selected from the group consisting of: Parkinson's Disease (idiopathic and genetic), Parkinson's Disease with dementia (PDD), multisystem atrophy (MSA), Frontotemporal Dementia, Dementia with Lewy Bodies (DLB), Gaucher's disease (GD), Neurodegeneration with Brain Iron Accumulation (NBIA), and neuroaxonal dystrophies (PLA2G6-associated neurodegeneration).

Embodiment 58. The method of embodiment 57, wherein the Parkinson's Disease is that wherein the patient has a mutation in one or more of the following genes: MAPT (Microtubule-associated protein tau), PRKN (parkin), PINK1 (PINK1), LRRK2 (leucine-rich repeat kinase 2), GBA (glucocerebrosidase), SNCA (alpha synuclein), PARK7 (DJ-1), and/or UCHL1 (ubiquitin carboxyl-terminal esterase L1).

Embodiment 59. The method of embodiment 56, wherein the tauopathy is selected from the group consisting of: Alzheimer's disease, dementia pugilistica, Guam Amyotrophic lateral sclerosis-Parkinsonism-Dementia (Guam ALS/PD), Pick Disease, Argyrophilic grain dementia, Nieman-Pick type C, Subacute sclerosing panencephalitis (SSPE), Progressive supranuclear palsy (PSP), multisystem atrophy (MSA), Corticobasoganlionic degeneration, Frontotemporal dementia with parkinsonism-17 (FTDP-17), Postencephalitic Parkinsonism (PEP), and Autosomal recessive Parkinsonism.

Embodiment 60. The method of embodiment 56, wherein the liver disease is selected from the group consisting of NASH/NAFL, pediatric NAFLD, alcoholic hepatitis, cholestatic liver disease, viral hepatitis, drug-induced liver toxicity, hemachromatosis, Wilson's disease, liver transplant reperfusion injury, hepatic insufficiency where the hepatic insufficiency is due to injury, SIRS, sepsis, or severe illness; and drug-induced liver toxicity, such as cisplatin-induced liver toxicity and acetaminophen-induced liver toxicity.

Embodiment 61. The method of embodiment 56, wherein the autistic spectrum disorder or pervasive developmental disorder is selected from the group consisting of autistic disorder, Asperger's syndrome, childhood disintegrative disorder (CDD), Rett's disorder, PDD-not otherwise specified (PDD-NOS), and attention deficit/hyperactivity disorder (ADHD).

Embodiment 62. The method of any one of embodiments 56-61, wherein the pharmaceutical composition is administered orally.

In certain embodiments, provided herein are methods of treating or suppressing a disease or disorder selected from the group consisting of an α-synucleinpathy, a tauopathy, an autistic spectrum disorder, a pervasive developmental disorder, a liver disease, liver damage, dementia, and reperfusion injury, comprising administering an pharmaceutical composition, as provided herein. In certain embodiments, provided herein are methods of treating or suppressing a disease or disorder selected from the group consisting of an α-synucleinpathy, a tauopathy, an autistic spectrum disorder, a pervasive developmental disorder, a liver disease, liver damage, dementia, and reperfusion injury, comprising administering an transdermal pharmaceutical composition, as provided herein.

In certain embodiments, provided herein are methods of using the pharmaceutical composition for treating or suppressing α-synucleinpathy. In certain embodiments, the α-synucleinpathy is selected from the group consisting of: Parkinson's Disease (idiopathic and genetic), Parkinson's Disease with dementia (PDD), multisystem atrophy (MSA), Frontotemporal Dementia, Dementia with Lewy Bodies (DLB), Gaucher's disease (GD), Neurodegeneration with Brain Iron Accumulation (NBIA), and neuroaxonal dystrophies (PLA2G6-associated neurodegeneration).

In certain embodiments, the Parkinson's Disease is that wherein the patient has a mutation in one or more of the following genes: MAPT (Microtubule-associated protein tau), PRKN (parkin), PINK1 (PINK1), LRRK2 (leucine-rich repeat kinase 2), GBA (glucocerebrosidase), SNCA (alpha synuclein), PARK7 (DJ-1), and/or UCHL1 (ubiquitin carboxyl-terminal esterase L1).

In certain embodiments, provided herein are methods of using the pharmaceutical composition for treating or suppressing tauopathy. In certain embodiments, the tauopathy is selected from the group consisting of: Alzheimer's disease, dementia pugilistica, Guam Amyotrophic lateral sclerosis-Parkinsonism-Dementia (Guam ALS/PD), Pick Disease, Argyrophilic grain dementia, Nieman-Pick type C, Subacute sclerosing panencephalitis (SSPE), Progressive supranuclear palsy (PSP), multisystem atrophy (MSA), Corticobasoganlionic degeneration, Frontotemporal dementia with parkinsonism-17 (FTDP -17), Postencephalitic Parkinsonism (PEP), and Autosomal recessive Parkinsonism.

In certain embodiments, provided herein are methods of using the pharmaceutical composition for treating or suppressing a liver disease or liver damage. In certain embodiments, the liver disease or liver damage is selected from the group consisting of NASH/NAFL, pediatric NAFLD, alcoholic hepatitis, cholestatic liver disease, viral hepatitis, drug-induced liver toxicity, hemachromatosis, Wilson's disease, liver transplant reperfusion injury, hepatic insufficiency where the hepatic insufficiency is due to injury, SIRS, sepsis, or severe illness; and drug-induced liver toxicity, such as cisplatin-induced liver toxicity and acetaminophen-induced liver toxicity.

In certain embodiments, provided herein are methods of using the pharmaceutical composition for treating or suppressing autistic spectrum disorder or pervasive developmental disorder. In certain embodiments, the autistic spectrum disorder or pervasive developmental disorder is selected from the group consisting of autistic disorder, Asperger's syndrome, childhood disintegrative disorder (CDD), Rett's disorder, PDD-not otherwise specified (PDD-NOS), and attention deficit/hyperactivity disorder (ADHD).

In certain embodiments, provided herein are methods for treating or suppressing dementia. In certain embodiments, the dementia is selected from the group consisting of vascular dementia, dementia associated with Huntington's disease, dementia associated with Creutzfeldt-Jakob disease, dementia associated with normal pressure hydrocephalus, dementia associated with Wernicke-Korsakoff syndrome, and dementia associated with posterior cortical atrophy (PCA).

In certain embodiments, provided herein are methods for treating or suppressing a disease or disorder selected from the group consisting of an α-synucleinpathy, a tauopathy, an autistic spectrum disorder, a pervasive developmental disorder, a liver disease, liver damage, dementia, and reperfusion injury, comprising orally administering a pharmaceutical composition provided herein.

Preparation of Compound 1

Compound 1 and its polymorph can be manufactured by methods known in the art, for example, Examples 1A, 1B, 2, 3A, and 3B as described in International Patent Application No. PCT/US2019/056836 (WO 2020/081879) which is incorporated by reference herein in its entirety, including any figures, for all purposes.

Manufacture of Pharmaceutical Compositions

Typical dosage forms are prepared according to the second aspect. In certain embodiments, step b) occurs at room temperature. In certain embodiments, step a) is mixing about 65:20:15 by weight of a pharmaceutically acceptable oil:a propylene glycol laurates composition:a polysorbate 80. In certain embodiments, step a) is mixing about 65:20:15 by weight of a Labrafac-like oil (Labrafac WL 1349):Lauroglycol 90:Tween 80. In certain embodiments, step a) is mixing about 65:20:20 by weight of a pharmaceutically acceptable oil:a propylene glycol laurates composition:a polysorbate 80. In certain embodiments, step a) is mixing about 65:20:20 by weight a Labrafac-like oil (Labrafac WL 1349):Lauroglycol 90:Tween 80. In certain embodiments, Compound 1 in step b) is a polymorph of an anhydrate of 2,3,5-trimethyl-6-nonylcyclohexa-2,5-diene-1,4-dione. In some embodiments, Compound 1 is measured under light protection or yellow light. In some embodiments, the formulation is added to a capsule. In some embodiments, the formulation solution is stored before encapsulation under light protection or yellow light. In some embodiments, the formulation is added to a capsule under light protection or yellow light.

Dosage and Unit Dosage Forms

In human therapeutics, the doctor will determine the posology which is considered most appropriate according to a treatment and according to the age, weight, stage of the infection and other factors specific to the subject to be treated. In certain embodiments, the pharmaceutical composition of the disclosure can be administered at the recommended maximum clinical dosage or at lower doses. Dosage levels of the active compounds in the compositions of the disclosure may be varied so as to obtain a desired response depending on the severity of the disorder and the response of the individual.

In certain embodiments, the pharmaceutical composition is administered for at least 24 weeks. In certain embodiments, the pharmaceutical composition is administered for at least 28 weeks. In certain embodiments, the pharmaceutical composition is administered at a dose selected from 150 mg BID and 250 mg BID. In certain embodiments, the pharmaceutical composition is administered at a dose of 150 mg BID. In certain embodiments, the pharmaceutical composition is administered at a dose of 250 mg BID. In certain embodiments, the pharmaceutical composition is administered at a dose selected from 100 mg BID and 500 mg BID. In certain embodiments, the pharmaceutical composition is administered at a dose of 100 mg BID. In certain embodiments, the pharmaceutical composition is administered at a dose of 500 mg BID. In certain embodiments, the pharmaceutical composition is administered at a dose of 10 capsules total for each day, wherein the weight of the pharmaceutical composition in each capsule is 50 mg for each day. In certain embodiments, the pharmaceutical composition is administered at a dose of 6 capsules total for each day, wherein the weight of the pharmaceutical composition in each capsule is 50 mg. In certain embodiments, the pharmaceutical composition is administered at dose ranging from about 100 mg to about 1000 mg daily dosage for a period of at least 14 days. The weights of Compound 1 provided in this paragraph do not include the weight of any water in a hydrate of Compound 1 or the weight of any solvent in a solvate of Compound 1.

In certain embodiments, the pharmaceutical composition administered dosages show no treatment emergent serious adverse events (TEAEs). In certain embodiments, the pharmaceutical composition administered dosages show no TEAEs leading to discontinuation of the pharmaceutical composition. In certain embodiments, the pharmaceutical composition administered dosages show no TEAEs leading to death.

Methods of Administration

The pharmaceutical compositions disclosed herein may be administered enterally, orally, sublingually, rectally, or topically in dosage unit formulations. In some embodiments, suitable modes of administration include oral, transdermal, transmucosal, iontophoretic, intraperitoneal, rectal, and gastrointestinal.

Oral administration is a preferred route of administration, and formulations suitable for oral administration are preferred formulations.

Oral administration may include administration in Low-fat Food. Oral administration may include administration in Medium-fat Food. Oral administration may include administration in food such as soft foods or semi-solid foods. Soft foods and semi-solid foods include applesauce, pudding (including chocolate), and jam or spread (including strawberry-flavored).

SEDDS formulations may be more amenable to administration via a feeding tube, as a feeding tube may be difficult to rinse with water. An advantage of the SEDDS formulations provided and claimed herein is that a feeding tube can be rinsed effectively with water. In certain embodiments, administration may be by feeding tube, at a dose of about 0.25 mL to about 10 mL, about 0.25 mL to about 7.5 mL, or about 2.5 mL, of a 100 mg/mL solution. In certain embodiments, administration may be by feeding tube, with a solution at a concentration of about 36 mg/mL to about 120 mg/mL. In certain embodiments, the dose is administered in a vehicle as provided in Formulations 1-6. In some or any embodiments, the ratio of oil to propylene glycol laurates composition to polysorbate 80 is about 65:20:15.

Topical administration is another preferred route of administration, and formulations suitable for topical administration are preferred formulations.

Formulations for topical administration may include lotions, tinctures, creams, emulsions, ointments, sprays, gels, and the like, and may further be formulated in other suitable formulations such as sunscreens, moisturizing lotions and creams, facial gels and creams, etc. Topical administration may also involve the use of transdermal administration such as transdermal patches or iontophoresis devices.

EXAMPLES

In the following examples, the abbreviations have the meanings provided in the table below.

| | |
|---|---|
| ADI | Allowable Daily Intake |
| DSE | Drug Safety Evaluation |
| FaSSIF | fasted State Simulated Intestinal Fluid |
| HLB | hydrophilic-lipophilic balance |
| o/w | oil/water or oil-in-water |
| RH | relative humidity |
| RRT | relative retention time |
| RT | room temperature |
| SEDDS | Self-Emulsifying Drug Delivery System |
| API | Active Pharmaceutical Ingredient |
| IIG | FDA Inactive ingredient Guide |
| TPGS | D-α-tocopheryl polyethylene glycol succinate |
| PO | By mouth |
| ICH | The International Council for Harmonisation |
| CRC | Child-resistant Cap |
| BE | Bioequivalent |
| Vehicle C | 60:20:20 Labrafac WL 1349:Lauroglycol 90:Tween 80 |
| Vehicle D | 65:20:15 Labrafac WL 1349:Lauroglycol 90:Tween 80 |

Certain densities are provided below where the vehicle for each is 65:20:15 Labrafac WL 1349, Lauroglycol 90, Tween 80:

| Solution | Density |
|---|---|
| 60 mg/mL solution | 961 mg/mL |
| 100 mg/mL solution | 962.9 mg/mL |
| vehicle (without Compound 1) | 959.9 mg/mL |

Densities were measured using procedures known to those of ordinary skill in the art.

Example 1

Screening of Solubilizers

Different solubilizers were screened for the formulation of Compound 1. Table 1 showed screening of excipients for the formulation of Compound 1. Compounds of Entries 6, 9, 11, 15, and 16 at both concentrations were soluble. Compounds of Entries 7 (200 mg/mL dilution), 8 (200 mg/mL dilution), and 17 (400 mg/mL dilution) were initially soluble but crashed out later (after overnight). Compounds of entries 1-5, 10, and 12-14, were not soluble. Gelucire 44/14 and Labrafac Lipo WL1349 seemed promising as solubilizers for Compound 1, and thus further experimentation were conducted with them (Entries 16 and 11 respectively). Although, caproyl also looked promising, it was found to be toxic in monkeys and thus, not pursued.

TABLE 1

Initial Screening of Potential Solubilizers for Compound 1

| Entry | Excipient | Initial Mass | 400 mg/mL dilution | add | 200 mg/mL dilution |
|---|---|---|---|---|---|
| 1 | PEG 400 | 500 | 1.25 | 1.25 | 2.50 |
| 2 | tween 80 | 500 | 1.25 | 1.25 | 2.50 |
| 3 | corn oil | 500 | 1.25 | 1.25 | 2.50 |
| 4 | cottonseed oil | 500 | 1.25 | 1.25 | 2.50 |
| 5 | span 80 | 500 | 1.25 | 1.25 | 2.50 |
| 6 | capryol PGMC | 500 | 1.25 | 1.25 | 2.50 |
| 7 | capryol 90 | 500 | 1.25 | 1.25 | 2.50 |
| 8 | lauroglycol 90 | 500 | 1.25 | 1.25 | 2.50 |
| 9 | lauroglycol FCC | 500 | 1.25 | 1.25 | 2.50 |
| 10 | plurol oleique CC 497 | 500 | 1.25 | 1.25 | 2.50 |
| 11 | labrafac lipo WL 1349 | 500 | 1.25 | 1.25 | 2.50 |
| 12 | labrasol | 500 | 1.25 | 1.25 | 2.50 |
| 13 | labrafil M1944CS | 500 | 1.25 | 1.25 | 2.50 |
| 14 | triethyl citrate | 500 | 1.25 | 1.25 | 2.50 |
| 15 | vitamin E TPGS | 500 | 1.25 | 1.25 | 2.50 |
| 16 | gelucire 44/14 | 500 | 1.25 | 1.25 | 2.50 |
| 17 | kolliphor HS 15 | 500 | 1.25 | 1.25 | 2.50 |

Based on the initial screening as shown in Table 1 and based on limits of excipients allowed by FDA, the solubility of Compound 1 in the oils in Table 1A were measured. Based on the solubility data, Labrafac WL 1349 was further pursued.

TABLE 1A

Solubility of Compound 1

| | Solubility, mg/mL | Temp, ° C. |
|---|---|---|
| Gelucire 44/14 | 269 | 45 |
| TPGS | 195 | 45 |
| PEG400 | 11 | 37 |
| Solutol HS15 | 94 | 37 |
| Sesame oil | 139 | RT |
| Olive oil | 135 | RT |
| Labrafac WL 1349 | Between 100 and 150 mg/g | RT |
| Soybean oil | <150 mg/g | RT |

Example 2

Screening of Gelucire Based Formulation

Certain combinations of Gelucire 44/14 with Solutol HS15, TPGS and Tween 80 were screened as shown in Table 2 at 200 mg/g concentration of Compound 1. Physical stability was observed microscopically at week one at 25° C./60% RH and at 5° C. Bioperformance was assessed visual observation after 10× dilution in FaSSIF. Based on the crash resistance test performed with ten times dilution with FaSSIF, the most promising formulation combination for Gelucire 44/14 appeared to be 80% w/w Gelucire 44/14, 10% w/w TPGS and 10% w/w Tween 80.

TABLE 2

Screening of Different Potential Gelucire-Based Formulations for Compound 1 at 200 mg/g Concentration (i.e. 200 mg of Compound 1 in 1 g of Compound 1 + vehicle)

| Component | % w/w | % w/w | % w/w | % w/w | % w/w | % w/w |
|---|---|---|---|---|---|---|
| Gelucire 44/14 | 85 | 80 | 90 | 90 | 80 | 70 |
| Solutol HS15 | 5 | — | — | — | — | — |
| TPGS | 5 | 10 | 10 | — | — | 10 |
| Tween 80 | 5 | 10 | — | 10 | 20 | 20 |
| Physical stability | Crystallization | Crystallization | Crystallization | Crystallization | Crystallization | Crystallization |
| Bioperformance | A lot of precipitation | Clear with minute crystals | A lot of precipitation | precipitates | precipitates | precipitates |

In the above table and in this paragraph, the % w/w are based on the total weight of the vehicle without compound. The 80% w/w Gelucire 44/14, 10% w/w TPGS and 10% w/w Tween 80 formulation vehicles were further tested at lower Compound 1 concentrations of 150 mg/g (i.e. 150 mg of Compound 1 in 1 g of Compound 1+vehicle) and 100 mg/g (i.e. 100 mg of Compound 1 in 1 g of Compound 1+vehicle) to minimize the crystallization risk upon storage. Physical stability was observed microscopically at week one at 25° C./60% RH and at 5° C. Bioperformance was assessed visual observation after 10× dilution in FaSSIF. As shown in Table 3, crystallization is observed after 1 h and 1.5 hour for Compound 1 concentrations of 150 mg/g (i.e. 150 mg of Compound 1 in 1 g of Compound 1+vehicle) and 100 mg/g (i.e. 100 mg of Compound 1 in 1 g of Compound 1+vehicle), respectively.

TABLE 3

Feasibility of Selected Gelucire-Based Formulation at Different Concentrations of Compound 1

| Component | Feasibility @ 150 mg/g % w/w | Feasibility @ 100 mg/g % w/w |
|---|---|---|
| Gelucire 44/14 | 80 | 80 |
| Solutol HS15 | — | — |
| TPGS | 10 | 10 |
| Tween 80 | 10 | 10 |
| Physical stability | Crystallization observed under microscope when compared to vehicle | Not clear from Microscope when compared to vehicle |
| Bioperformance risk | A lot of precipitation at RT within 1 h | Clear up to 1 h, Started seeing precipitation at RT after 1.5 h |

In the above table, the % w/w are based on the total weight of the vehicle without compound.

Example 3

Screening of Labrafac-Based Formulation

To develop a SEDDS formulation of Compound 1, the combinations of Labrafac WL 1349 with co-surfactant Lauroglycol 90 (low HLB value) and surfactant Tween 80 (High HLB value) were tested to form a SEDDS formulation (Table 4).

TABLE 4

Labrafac-Based SEDDS considered for Compound 1

| Component | Formulation A % w/w | Formulation B % w/w |
|---|---|---|
| Labrafac WL 1349 | 60 | 80 |
| LauroGlycol | 20 | 10 |
| Tween 80 | 20 | 10 |

In the above table, the % w/w are based on the total weight of the vehicle without compound. Formulation A formed a clear single phase solution vehicle whereas Formulation B did not form a single phase with Tween 80 forming a separate phase.

Formulation A was further evaluated as potential SEDDS formulation of Compound 1.

Example 4

Comparison of Gelucire-Based vs. Labrafac Based Formulations

The Gelucire 44/14 formulation in Table 5 was prepared by melting at 45° C. and mixing the required quantities of TPGS (melted at 37° C.) and Tween 80 at RT to form a clear solution vehicle at 45° C. Compound 1 was then solubilized by mixing at 45° C. to form a clear solution.

The Labrafac-based formulation in Table 5 was prepared by mixing Labrafac WL 1349 with Lauroglycol 90 and Tween 80 at RT to form a clear solution vehicle. Compound 1 was then solubilized by mixing advantageously at RT to form a clear solution. In the table below, the % w/w are based on the total weight of the vehicle without compound.

Two formulations selected for Gelucire 44/14-based and Labrafac-WL-1349-based formulation vehicles with Compound 1 at 100 mg/g (i.e. 100 mg of Compound 1 in 1 g of Compound 1+vehicle) are shown and compared in Table 5. The Gelucire 44/14-based formulation is a semi-solid at RT, while the Labrafac-WL-1349-based formulation is advantageously a liquid at RT. The Gelucire 44/14-based formulation, when diluted to 10 times with FaSSIF, forms a clear solution. However, Compound 1 precipitation is observed after about 1.5 hour. The Labrafac-WL-1349-based formulation forms an oil-in-water emulsion when diluted to 10 times with water, and Compound 1 is crash-resistant for at least about 24 hours, being predominantly solubilized in the oil phase.

TABLE 5

Comparison of Gelucire-Based and Labrafac-Based Formulations for Compound 1 (100 mg/g) (i.e. 100 mg of Compound 1 in 1 g of Compound 1 + vehicle)

| Gelucire Vehicle 1 | | Vehicle C | |
|---|---|---|---|
| Component | % w/w | Component | % w/w |
| Gelucire 44/14 | 80 | Labrafac WL 1349 | 60 |
| TPGS | 10 | LauroGlycol | 20 |
| Tween 80 | 10 | Tween 80 | 20 |
| Water soluble components and thus forms a clear solution upon dilution | | Oil based formulation and thus forms an o/w emulsion upon dilution in water | |
| Upon 10X dilution in FaSSIF, the API is crash resistant up to 1.5 h | | Upon 10 X dilution in water, the API is crash resistant up to 24 h with API predominantly solubilized in the oil phase | |
| Semi-solid formulation at RT | | Liquid formulation at RT | |
| Physically unstable at RT within 1 month | | Physically stable at RT up to 1 month | |
| Chemically stable at 25° C./60% RH and 40° C./75% RH for 1 month | | Chemically stable at 25° C./60% RH and 40° C./75% RH for 1 month | |

Example 4A

Physical stability evaluation of both Gelucire 44/14-based and Labrafac-WL-1349-based formulation vehicles was done under polarized microscope. The Gelucire 44/14-based formulation as shown in FIG. 1 clearly crystallized out at 25° C./60% RH at one month with liquid phase separation observed visually. Hence, the Gelucire 44/14 -based formulation was physically unstable upon storage for one month. The Labrafac-WL-1349-based formulation as shown in FIG. 2 was still a clear solution with no birefringent crystals observed both at 25 ° C./60% RH and 40° C./75% RH for at one month. Therefore, Labrafac-WL-1349-based formulation was physically stable upon storage.

Example 4B

The chemical stability evaluation were also performed. Both Gelucire 44/14-based and Labrafac-WL-1349-based formulations are chemically stable at 25° C./60% RH and 40° C./75% RH at one month with less than 0.05 percentage points of degradation observed in either formulations as shown in Table 6 and 7 respectively.

Based on the solubility, and physical stability data, the Labrafac-WL-1349-based formulation was further pursued, and discussed herein.

TABLE 6

Chemical Stability of Selected Gelucire-Based Formulation of Compound 1 at 100 mg/g Concentration (i.e. 100 mg of Compound 1 in 1 g of Compound 1 + vehicle)

| | % | % Impurity (% Area) | | | | | | |
|---|---|---|---|---|---|---|---|---|
| Sample Id | Assay (% LC) | RRT 0.66 | RRT 0.78 | RRT 0.80 | RRT 0.94 | Compound 1 | RRT 1.44 | Total % Impurity |
| Initial | 100.8 | 0.06 | 0.05 | 0.13 | 0.08 | 99.68 | | 0.32 |
| 1 M_RT | 101.1 | 0.06 | 0.04 | 0.18 | 0.08 | 99.60 | 0.03 | 0.39 |
| 1 M_40° C./75% RH | 102.2 | 0.06 | 0.04 | 0.14 | 0.09 | 99.62 | 0.04 | 0.37 |

In the above table, 1M means 1 month.

TABLE 7

Chemical Stability of Selected Labrafac-WL-1349-Based Formulation of Compound 1 at 100 mg/g Concentration (i.e. 100 mg of Compound 1 in 1 g of Compound 1 + vehicle)

| | % | % Impurity (% Area) | | | | | | |
|---|---|---|---|---|---|---|---|---|
| Sample Id | Assay (% LC) | RRT 0.66 | RRT 0.78 | RRT 0.80 | RRT 0.94 | Compound 1 | RRT 1.44 | Total % Impurity |
| Initial | 101.3 | 0.06 | 0.05 | 0.12 | 0.08 | 99.69 | | 0.31 |
| 1 M_RT | 100.6 | 0.06 | 0.03 | 0.08 | 0.08 | 99.71 | 0.03 | 0.28 |
| 1 M_40° C./75% RH | 101.5 | 0.07 | 0.04 | 0.05 | 0.08 | 99.73 | 0.04 | 0.27 |

In the above table, 1M means 1 month.

Example 5

Stability of Labrafac-WL-1349-Based Formulation Compared to Sesame Oil-Based Formulation A sesame oil formulation was prepared by mixing 100 mg Compound 1 per g of Compound 1 and sesame oil.

The physical and chemical stability of Vehicle C Labrafac-WL-1349-based formulation of Compound 1 at 100 mg/g and sesame oil-based formulation were performed.

Both formulations were physically stable for up to 3 months at 25° C./60% RH and 40° C./75% RH conditions with no birefringent crystals observed under polarized microscope (data not shown).

As shown in Table 8, the formulation was relatively stable with total impurity levels increasing only from 0.31% at initial to 0.38% at three months at 40° C./75% RH. Table 10 showed the formulation vehicle used.

TABLE 8

Chemical Stability of Labrafac-WL-1349-Based Formulation of Compound 1 at 100 mg/g Concentration (i.e. 100 mg of Compound 1 in 1 g of Compound 1 + vehicle) up to 6 months and of Sesame Oil-based Formulation of Compound 1 at 100 mg/g Concentration (i.e. 100 mg of Compound 1 in 1 g of Compound 1 + vehicle) up to 3 months

| Sample Id | % Assay (% LC) | RRT 0.19 | RRT 0.66 | RRT 0.78 | RRT 0.80 | RRT 0.85 | RRT 0.94 | Cmpd 1 | RRT 1.44 | RRT 1.46 | Total % Impurity |
|---|---|---|---|---|---|---|---|---|---|---|---|
| Initial | 101.3 | ND | 0.06 | 0.05 | 0.12 | ND | 0.08 | 99.69 | ND | ND | 0.31 |
| 1 M 25° C./60% RT | 100.6 | ND | 0.06 | 0.03 | 0.08 | ND | 0.08 | 99.71 | 0.03 | 0.03 | 0.28 |
| 3 M 25° C./60% RT | 103.4 | ND | 0.07 | ND | 0.04 | ND | 0.08 | 99.72 | 0.06 | 0.03 | 0.28 |
| 6 M 25° C./60% RT | 101.7 | 0.02 | 0.06 | 0.02 | 0.04 | 0.03 | 0.08 | 99.64 | 0.07 | 0.04 | 0.36 |
| 1 M 40° C./75% RH | 101.5 | ND | 0.07 | 0.03 | 0.05 | ND | 0.08 | 99.73 | 0.04 | 0.04 | 0.27 |
| 3 M 40° C./75% RH | 102.5 | 0.04 | 0.06 | ND | 0.04 | 0.04 | 0.07 | 99.61 | 0.08 | 0.05 | 0.38 |
| 6 M 40° C./75% RH | 100.8 | 0.05 | 0.05 | ND | 0.04 | 0.04 | 0.07 | 99.58 | 0.09 | 0.07 | 0.41 |

In the above table, 1M, 3M, and 6M means 1 month, 3 months and 6 months respectively.

In the above table, 1M and 3M means 1 month and 3 months respectively.

Example 6

ADI Limits for Labrafac-WL-1349-Based Formulation Components

The Allowable Daily Intake (ADI) values for each of the excipients or components of the Labrafac-WL-1349-based Formulation C-1 is shown in Table 9. At the maximum possible clinical dose of 1000 mg/day of Compound 1, the ADI limit for Vehicle C is exceeded for Tween 80 (1800 mg vs. 1500 mg ADI limit). Labrafac WL 1349 and Lauroglycol 90 levels are well within the limit at this highest dose level. The Tween 80 level was reduced from 20% w/w to 15% w/w in the vehicle (Vehicle D) to keep within the ADI limits. The composition of an optimized Vehicle D is Labrafac WL 1349 65% w/w, Lauroglycol 90 20% w/w and Tween 80 15% w/w. This vehicle still forms a clear single-phase solution at RT.

TABLE 8a

Chemical Stability of Sesame Oil-based Formulation of Compound 1 at 100 mg/g Concentration (i.e. 100 mg of Compound 1 in 1 g of Compound 1 + vehicle) up to 3 months

| Sample Id | % Assay (% LC) | RRT 0.66 | RRT 0.68 | RRT 0.76 | RRT 0.78 | RRT 0.80 | RRT 0.94 | Cmpd 1 | RRT 1.42 | RRT 1.44 | RRT 1.46 | Total % Impurity |
|---|---|---|---|---|---|---|---|---|---|---|---|---|
| Initial | 103.6 | 0.06 | ND | 0.03 | 0.04 | 0.14 | 0.09 | 99.62 | ND | 0.03 | ND | 0.39 |
| 1 M 25° C./60% RT | 100.7 | 0.06 | ND | 0.02 | 0.04 | 0.18 | 0.08 | 99.58 | ND | 0.03 | ND | 0.41 |
| 3 M 25° C./60% RT | 101.6 | 0.06 | 0.06 | ND | 0.04 | 0.17 | 0.08 | 99.43 | 0.05 | 0.06 | 0.04 | 0.56 |
| 1 M 40° C./75% RH | 99.9 | 0.06 | ND | 0.03 | 0.04 | 0.17 | 0.08 | 99.57 | ND | 0.04 | ND | 0.42 |
| 3 M 40° C./75% RH | 101.8 | 0.06 | 0.06 | 0.03 | 0.04 | 0.16 | 0.09 | 99.37 | 0.03 | 0.09 | 0.06 | 0.62 |

TABLE 9

ADI Limits for Excipients in Labrafac-WL-1349-
Based Formulation C-1 Based on Input From DSE

| Ingredient | IIG | ADI (mg/kg/day) | | ADI (mg/day) | Formulation Formulation C-1 | 250 mg per day | 500 mg per day | 1000 mg per day |
|---|---|---|---|---|---|---|---|---|
| Cmpd 1 | | | | | 100 mg/g | NA | NA | NA |
| Labrafac WL 1349 (Gattefosse)/ medium-chain triglycerides | 3390/ 5 mL | 90[a] | Calculated from 47 week rat data. | 5400 | 540 | 1350 | 2700 | 5400 |
| Lauroglycol 90 (Gattefosse)/ Propylene glycol monolaurate | 235 mg | 500[b] | EU limit for food additive | 30000 | 180 | 450 | 900 | 1800 |
| Tween 80 (Croda)/ Polysorbate 80 | 418 mg | 25 | EU, FDA limit for food additive | 1500 | 180 | 450 | 900 | 1800 |
| Total | | | | | 1000 | NA | NA | NA |

[a]The ADI is calculated based on NOAEL of 9 g/kg from 47 weeks study in Wister rats using procedures disclosed in *Food Chem Toxicol.* 2000, 38(1), 79-98.
[b]The ADI is 500 mg/kg per day for adult patients and children >5 years and 50 mg/kg for children <5 years and >1 month.

The IIG values in Table 10 are the limits of the excipients on the FDA website.

The actual compositions of Compound 1 (at 100 mg/g concentration, i.e. 100 mg of Compound 1 in 1 g of Compound 1+vehicle) with 18% Tween 80 (60:20:20 Labrafac-WL-1349:Lauroglycol 90:Tween 80) (Formulation C-1) and 13.5% Tween 80 (65:20:15 Labrafac-WL-1349:Lauroglycol 90:Tween 80) (Formulation D-1) are shown in Table 10 and Table 11, respectively.

TABLE 10

Composition of Compound 1 in the Vehicle C
Formulation C-1

| Components | % w/w | % w/w |
|---|---|---|
| Compound 1 | 10 | — |
| Labrafac WL 1349 | 54 | 60% |
| Lauroglycol 90 | 18 | 20% |
| Tween 80 | 18 | 20% |

TABLE 11

Composition of Compound 1 in the Vehicle D
Formulation D-1

| Components | % w/w | % w/w |
|---|---|---|
| Compound 1 | 10 | — |
| Labrafac WL 1349 | 58.5 | 65% |
| Lauroglycol 90 | 18 | 20% |
| Tween 80 | 13.5 | 15% |

The actual compositions of Compound 1 (at 60 mg/mL concentration) with 14.07% Tween 80 (65:20:15 Labrafac-WL-1349:Lauroglycol 90:Tween 80) (Formulation E-1) and Compound 1 (at 100 mg/mL concentration) with 13.44% Tween 80 (65:20:15 Labrafac-WL-1349:Lauroglycol 90:Tween 80) (Formulation F-1) are shown in Table 12 and Table 13, respectively.

TABLE 12

Composition of Compound 1 in the Vehicle E
Formulation E-1

| Components | % w/w | % w/w without Compound 1 |
|---|---|---|
| Compound 1 | 6.243 | — |
| Labrafac WL 1349 | 60.94 | 65% |
| Lauroglycol 90 | 18.75 | 20% |
| Tween 80 | 14.07 | 15% |

TABLE 13

Composition of Compound 1 in the Vehicle F
Formulation F-1

| Components | % w/w | % w/w without Compound 1 |
|---|---|---|
| Compound 1 | 10.39 | — |
| Labrafac WL 1349 | 58.25 | 65% |
| Lauroglycol 90 | 17.92 | 20% |
| Tween 80 | 13.44 | 15% |

Example 7

Stability of 50 mg and 60 mg Strength Capsules Prepared from 100 mg/g (Formulation D-1) and 120 mg/g (Formulation D-2) Concentrations, Respectively The physical and chemical stability of 50 mg strength capsules of Formulation D-1 (100 mg/g concentration in Vehicle D, i.e. 100 mg of Compound 1 in 1 g of Compound 1 + Vehicle D) was assessed at accelerated conditions of temperature and humidity. The physical and chemical stability of 60 mg strength capsules of Compound 1 Formulation D-2 (120 mg/g concentration in Vehicle D, i.e. 100 mg of Compound 1 in 1 g of Compound 1+Vehicle D) was also assessed at accelerated conditions of temperature and humidity. Size 00 Hard Gelatin Capsules of Swedish orange color were used for the study.

Both strengths are physically stable for up to one month at 5° C., 25° C./60% RH and 40° C./75% RH conditions with no birefringent crystals observed under polarized microscope (data not shown).

Example 8

Chemical Stability of Formulation in Capsules

The chemical stability of 50 mg and 60 mg strength capsules of Compound 1 Labrafac-based Formulations D-1 and D-2, respectively, analyzed by HPLC, is shown in Table 14 and Table 15, respectively. About 2% or less change in potency from initial to a duration of time of at least one month at 5° C., 25° C./60% RH and 40° C./75% RH for both strengths were observed. Also, about 1 percentage point or less degradation was observed from initial to all conditions tested for both strengths.

TABLE 14

Chemical Stability of Formulation D-1 (50 mg Strength Capsules of Compound 1 in Vehicle D (15% Tween 80 based on weight of vehicle) at 100 mg/g Concentration) up to three months

| Sample Id | % Assay (% LC) | % Impurity (% Area) | | | | | | | | |
|---|---|---|---|---|---|---|---|---|---|---|
| | | RRT 0.66 | RRT 0.76 | RRT 0.78 | RRT 0.79 | RRT 0.80 | RRT 0.94 | Compound 1 | RRT 1.46 | Total % Impurity |
| Initial | 98.4 | 0.06 | 0.04 | 0.03 | 0.02 | 0.18 | 0.08 | 99.56 | 0.03 | 0.44 |
| 1 M_5 C. | 100.9 | 0.06 | 0.04 | 0.02 | 0.03 | 0.17 | 0.08 | 99.58 | 0.03 | 0.43 |
| 3 M_5 C. | 101.8 | 0.06 | 0.02 | 0.04 | 0.03 | 0.18 | 0.08 | 99.54 | 0.03 | 0.44 |
| 1 M_25 C./60% RH | 100.2 | 0.06 | 0.04 | ND | 0.03 | 0.18 | 0.09 | 99.57 | 0.03 | 0.43 |
| 3 M_25 C./60% RH | 100.1 | 0.06 | 0.02 | 0.05 | 0.03 | 0.17 | 0.08 | 99.55 | 0.03 | 0.44 |
| 1 M_40 C./75% RH | 99.7 | 0.06 | 0.04 | ND | 0.03 | 0.17 | 0.08 | 99.57 | 0.04 | 0.42 |
| 3 M_40 C./75% RH | 100.1 | 0.07 | 0.02 | 0.04 | 0.03 | 0.12 | 0.09 | 99.57 | 0.05 | 0.42 |

TABLE 15

Chemical Stability of Formulations D-2 (60 mg Strength Capsules of Compound 1 in Vehicle D (15% Tween 80 based on weight of vehicle) at 120 mg/g Concentration) up to three months

| Sample Id | % Assay (% LC) | % Impurity (% Area) | | | | | | | | | |
|---|---|---|---|---|---|---|---|---|---|---|---|
| | | RRT~ 0.19 | RRT~ 0.66 | RRT~ 0.76 | RRT~ 0.78 | RRT~ 0.79 | RRT~ 0.80 | RRT~ 0.94 | Cmpd 1 | RRT~ 1.44 | RRT~ 1.46 | Total % Impurity |
| Initial | 102.7 | ND | 0.06 | 0.04 | 0.02 | 0.02 | 0.18 | 0.08 | 99.57 | ND | 0.03 | 0.43 |
| 1 M_5 C. | 100.7 | ND | 0.06 | 0.02 | 0.04 | 0.03 | 0.20 | 0.07 | 99.55 | ND | 0.03 | 0.45 |
| 3 M_5 C. | 101.2 | ND | 0.06 | 0.02 | 0.04 | 0.02 | 0.20 | 0.08 | 99.48 | 0.04 | 0.05 | 0.51 |
| 1 M_25 C./60% RH | 100.8 | ND | 0.06 | 0.03 | 0.04 | 0.03 | 0.18 | 0.08 | 99.55 | ND | 0.03 | 0.45 |
| 3 M_25 C./60% RH | 99.0 | ND | 0.06 | 0.02 | 0.04 | 0.03 | 0.18 | 0.08 | 99.49 | 0.04 | 0.05 | 0.50 |
| 1 M_40 C./75% RH | 101.2 | ND | 0.06 | 0.02 | 0.04 | 0.03 | 0.17 | 0.08 | 99.56 | ND | 0.04 | 0.44 |
| 3 M_40 C./75% RH | 100.3 | 0.03 | 0.06 | 0.02 | 0.04 | 0.03 | 0.14 | 0.08 | 99.51 | 0.04 | 0.05 | 0.49 |

Example 9

Chemical Stability of Formulation Solutions

The chemical stability of 60 mg/mL and 100 mg/mL strengths of Compound 1 Labrafac-WL-1349-based Formulations E-1 and F-1, respectively, analyzed by HPLC, is shown in Table 16 and Table 17, respectively. No change in potency was detected from initial measurement to a measurement at two weeks or at one month, for each of the two test conditions (25° C./60% RH and 40° C./75% RH. In addition, no degradation was observed from initial to all conditions tested for both solutions.

TABLE 16

Chemical Stability of Formulation E-1 (at 60 mg/mL Concentration of Compound 1 - Labrafac-WL-1349-Based Formulation) up to three months
Compound 1 Oral Solution 60 mg/mL

| Sample Id | Appearance | % Assay | % Impurity Individual unspecified | % Impurity Total | Water Content (%) | Water Activity (aw) |
|---|---|---|---|---|---|---|
| Initial | Clear yellow liquid | 101.0 | ND | ND | 0.04 | 0.1685 |
| 2 W_25° C./60% RH | Clear yellow liquid | 101.5 | ND | ND | 0.18 | — |
| 1 M_25° C./60% RH | Clear yellow liquid | 101.5 | ND | ND | 0.07 | — |
| 2 W_40° C./75% RH | Clear yellow liquid | 100.8 | ND | ND | 0.13 | — |
| 1 M_40° C./75% RH | Clear yellow liquid | 101.9 | ND | ND | 0.09 | — |

TABLE 17

Chemical Stability of Formulation F-1 (at 100 mg/mL Concentration of Compound 1 - Labrafac-WL-139-Based Formulation) up to three months
Compound 1 Oral Solution 100 mg/mL

| Sample Id | Appearance | % Assay | % Impurity Individual unspecified | % Impurity Total | Water Content (%) | Water Activity (aw) |
|---|---|---|---|---|---|---|
| Initial | Clear yellow liquid | 100.5 | ND | ND | 0.05 | 0.1710 |
| 2 W_25 C./60% RH | Clear yellow liquid | 100.1 | ND | ND | 0.16 | — |
| 1 M_25 C./60% RH | Clear yellow liquid | 100.9 | ND | ND | 0.08 | — |
| 2 W_40 C./75% RH | Clear yellow liquid | 99.8 | ND | ND | 0.17 | — |
| 1 M_40 C./75% RH | Clear yellow liquid | 100.6 | ND | ND | 0.07 | — |

Example 10

Monkey PK Study

A monkey PK study was conducted with a sesame oil formulation of 100 mg/g of Compound 1, a Gelucire 44/14-based formulation of 100 mg/g Compound 1 (Gelucire Form 1), and two different Labrafac-WL-1349-based formulations of 100 mg/g Compound 1. In this paragraph, 100 mg/g is 100 mg of Compound 1 in 1 g of Compound 1+vehicle. The formulations were administered with Low-fat Food for Testing and Medium-fat Food for Testing and Labrafac-WL-1349-based formulation of Compound 1 administered with Low-fat Food for Testing at dose of 125 mg, PO (Table 18). Each of the formulations in Table 18 were administered as 4 capsules/dose. In the table below, the % w/w are based on the total weight of the vehicle without compound. Four monkeys per cohort were used.

TABLE 18

Monkey PK Study Design for Compound 1 Formulations

| Formulations: | Meal |
|---|---|
| P1G1: Sesame oil solution | Medium Fat Food for Testing |
| P2G1: Gelucire Vehicle 1 (80 w/w % Gelucire 44/14, 10 w/w % TPGS and 10 w/w % Tween 80) | Medium Fat Food for Testing |
| PO1: Labrafac Vehicle C (60 wt/wt % Labrafac WL 1349, 20 wt/wt % Lauroglycol 90, 20 wt/wt % Tween 80) | Low Fat Food for Testing |
| P1G2: Vehicle C (60 wt/wt % Labrafac WL 1349, 20 wt/wt % Lauroglycol 90, 20 wt/wt % Tween 80) | Medium Fat Food for Testing |
| PO2: Vehicle D (65 wt/wt % Labrafac WL 1349, 20 wt/wt % Lauroglycol 90, 15 wt/wt % Tween 80) | Low Fat Food for Testing |
| PO3: Vehicle D (65 wt/wt % Labrafac WL 1349, 20 wt/wt % Lauroglycol 90, 15 wt/wt % Tween 80) | Medium Fat Food for Testing |

Low Fat: 11.4% fat (by calories), about 34 kcal
Medium Fat: 37.9% fat (by calories), about 62 kcal
Dose: 125 mg PO Single Dose As shown in Table 19, bioavailability appears to be superior for Gelucire 44/14-based formulation (60.0%). Bioavailability of Labrafac-based formulation P1G2 (49.1%) is comparable to sesame oil-based formulation P1G1 (~40.8%) with Labrafac formulation P1G2 having slightly higher exposure at 49.1%. Another observation is the absence of a second peak in the PK profiles of Gelucire 44/14-based and Labrafac-based formulations of Compound 1 compared to 2sesame oil-based formulation. This second peak in the sesame oil formulation indicates an unknown absorption phenomenon.

Also as shown in Table 19, better mitigation of observed positive food effect (i.e. a smaller difference in bioavailability between an administration with Low-fat Food for Testing and an administration with Medium-fat Food for Testing) is best with Labrafac-WL-1349-based formulation with Vehicle D (where the vehicle alone contains 15 wt/wt % Tween 80) compared to Labrafac-WL-1349-based formulation with Vehicle C (where the vehicle alone contains 20 wt/wt % Tween 80). With a low-fat meal, the Labrafac-WL-1349-based formulation with Vehicle D (where the vehicle alone contains 15 wt/wt % Tween 80) has a comparable bioavailability to Labrafac-WL-1349-based formulation with Vehicle C (where the vehicle alone contains 20 wt/wt % Tween 80). However, with Medium Fat Food for Testing, a formulation using Vehicle D has a lower bioavailability of 29.4% compared to 49.1% bioavailability obtained with a formulation using Vehicle C. Thus, the lesser difference in bioavailability between Low Fat Food for Testing and Medium Fat Food for Testing for Vehicle D (15% Tween 80) when compared to Vehicle C (20% Tween 80) is surprising. This means that a formulation of Compound 1 in Vehicle D could be administered advantageously with or without food. In the table below, the wt/wt % refers to the amount of Tween in the vehicle (without compound).

TABLE 19

Monkey PK Study Results (PK Parameters) for Various Formulations of Compound 1 (administered PO, 125 mg)

| Formulation | Food (Fat %) | $T_{1/2}$ (h) | Tmax (h) | Cmax (h) | $AUC_{last}$ (h*ng/mL) | $AUC_{0-24\,h}$ (h*ng/mL) | $C_{avg,\,0-24\,h}$ (ng/mL) | $C_{24\,h}$ (ng/mL) | F** (%) |
|---|---|---|---|---|---|---|---|---|---|
| Sesame Solution* (P1G1) | 37.9% | 6.94 | 5.3 | 2080 | 10800 | 10200 | 416 | 77.8 | 40.8 |
| Gelucire 44/14 (P2G1) | | 8.25 | 4.0 | 4050 | 15800 | 15400 | 641 | 43.4 | 60.0 |
| 20 wt/wt % Tween (PO1) | 11.4% | 5.60 | 4.0 | 742 | 3220 | 3220 | 134 | 10.5 | 13.4 |
| 20 wt/wt % Tween (P1G2) | 37.9% | 8.87 | 4.5 | 2690 | 12900 | 12600 | 524 | 37.7 | 49.1 |
| 15 wt/wt % Tween (PO2) | 11.4% | 7.25 | 4.0 | 689 | 3040 | 3010 | 125 | 13.6 | 14.0 |
| 15 wt/wt % Tween (PO3) | 37.9% | 5.15 | 4.0 | 1110 | 5660 | 5660 | 236 | 17.2 | 29.4 |

*One animal was excluded from the calculation;
**F calculated relative to IV dose of 0.5 mg/kg (1.3 mg) in Study II (doses were adjusted for B.Wt).
a: $T_{last}$ 16.5 hr; b: $T_{last}$ 14.0 hr.

Example 10a

Solubility Screening of Additional Pharmaceutically Acceptable Oils ("oils"), Surfactants and Co-Surfactants A total of 36 different excipients including pharmaceutically acceptable oils, surfactants and co-surfactants were evaluated for Compound 1. Solubility is as shown in Table 20. Higher solubility of Compound 1 in oils is desirable to increase drug loading.

TABLE 20

SEDDS Excipient Solubility Screening Studies

| | Component | Solubility mg/mL | Temperature | |
|---|---|---|---|---|
| Glycerides | Sesame Oil | 139 | RT | Oils |
| | Olive Oil | 135 | RT | |
| | Soybean Oil | 110.59 | RT | |
| | Corn Oil | 115.34 | RT | |
| | Cottonseed Oil | 111.76 | RT | |
| | Maisine CC | 90.34 | RT | |
| | Pe Ceol | IIG of 0.8 mg | | |
| | Labrafac Lipo WL1349 | 140.92 | RT | |
| | Labrafac PG | 221.91 | RT | |
| | Labrafac MC60 | Semi-sloid | | |
| | Castor Oil | Laxative | | |
| | Peanut Oil | Non-GMP | | |

TABLE 20-continued

SEDDS Excipient Solubility Screening Studies

| | Component | Solubility mg/mL | Temperature | |
|---|---|---|---|---|
| Polyglycerol esters | Plurol oleique CC 497 | 50-100 (range) | | Co-surfactants |
| Propylene glycol esters | Lauroglycol FCC | 159.7 | RT | |
| | Capryol PGMC | 183.74 | RT | |
| | Capryol 90 | 124.54 | RT | |
| | Lauroglycol 90 | 133.48 | RT | |
| Polyoxyglycerides PEG esters | Labrafil M1944CS | 100.75 | RT | Water Dispersible Surfactant |
| | Labrafil M2125CS | 118.61 | RT | |
| | Labrafil M2130CS | Solid[2] | | |
| | Labrasol | 35.73 | RT | |
| | TPGS | 195 | 45 | |
| | Gelucire 44/14 | 269 | 45 | |
| | Gelucire 48/16 | Solid | | |
| | Gelucire 50/13 | Solid | | |
| Additional Surfactants | Tween 80 | 25-50 (range) | | Other Surfactant |
| | Tween 20 | Not Filterable | | |
| | Tween 40 | Non-GMP | | |
| | | Non-GMP | | |
| | Tween 60 | 50-100 (range) | | |
| | Span 80 | Solid | | |
| | Span 20 | Non-GMP | | |
| | Span 60 | Non-GMP | | |
| | Triethyl citrate | 30.06 | RT | |
| | Poloxamer 124 | Non-GMP | | |
| | Poloxamer 331 | Non-GMP | | |

SEDDS Formulation Screening: Phase Clarity and Solubility Studies

As shown in Table 20, the SEDDS formulation can be achieved with a range of pharmaceutically acceptable oils. However, the choice of surfactant and co-surfactant may be limited due to several reasons: (a) some commercially available surfactants are non-GMP in nature and hence cannot be used for humans, (b) semi-solid physical state of some of the excipients makes them inappropriate for oral solution formulation, and/or (c) phase miscibility issues with some surfactants causing physical instability including drug precipitation. In order to achieve an optimized SEDDS formulation of a combination of oil, surfactant, and co-surfactant. Several formulation design related aspects are considered, for example: safe amount for daily intake for excipients, drug solubility in SEDDS formulations, crash resistance/drug precipitation, physical and chemical stability, bioperformance, and pharmacokinetics. Based on these aforementioned criteria, two co-surfactants (Lauroglycol 90 and Capryol 90) and a surfactant (Tween 80) were selected to prepare additional SEDDS formulations. Sesame oil only formulation exhibited a second peak as shown in FIG. 3.

A total of 15 SEDDS formulations were screened for the phase clarity and solubility studies as shown in Table 21. In the table below, the % w/w are based on the total weight of the vehicle without compound. Most of the SEDDS formulations (e.g., olive-oil based, Labrafac-WL-1349-based etc.) were clear and provided high drug solubility. Highest solubility of Compound 1 was observed with Labrafac PG and Labrafac WL 1349 based formulations. The SEDDS formulations that exhibited hazy or had significantly lower drug solubility were omitted from further screening. Hence, a total of 6 formulations (Table 21, Prototype # 4, 6, 10, 12, 14, and 15) were selected for a monkey PK study.

TABLE 21

Compositions of SEDDS Formulations Evaluated in Monkey PK Study

| | Excipient Components | | | Observations | |
|---|---|---|---|---|---|
| Proto-type | Oil Solubilizer (65% wt/wt) | Co-surfactant (20% wt/wt) | Surfactant (15% wt/wt) | Visual Clarity | Compound 1 Solubility (mg/mL at RT) |
| 1 | Maisine CC | Capryol 90 | Tween 80 | Clear | 108.54 |
| 2 | Maisine CC | Lauroglycol 90 | Tween 80 | Clear | 103.85 |
| 3 | Olive Oil | Capryol 90 | Tween 80 | Clear | 130.2 |
| 4 | Olive Oil | Lauroglycol 90 | Tween 80 | Clear | 135.32 |
| 5 | Corn Oil | Capryol 90 | Tween 80 | Hazy | NA |
| 6 | Corn Oil | Lauroglycol 90 | Tween 80 | Clear | 131.45 |
| 7 | Sesame Oil | Capryol 90 | Tween 80 | Hazy | NA |
| 8 | Sesame Oil | Lauroglycol 90 | Tween 80 | Clear | 136.13 |
| 9 | Labrafac WL 1349 | Capryol 90 | Tween 80 | Clear | 129.08 |
| 10 | Labrafac WL 1349 | Lauroglycol 90 | Tween 80 | Clear | 176.2 |
| 11 | Soybean Oil | Capryol 90 | Tween 80 | Hazy | NA |
| 12 | Soybean Oil | Lauroglycol 90 | Tween 80 | Clear | 128.17 |
| 13 | Cottonseed Oil | Capryol 90 | Tween 80 | Hazy | NA |
| 14 | Cottonseed Oil | Lauroglycol 90 | Tween 80 | Clear | 132.47 |
| 15 | Labrafac PG | Lauroglycol 90 | Tween 80 | Clear | 233.10 |

The six formulations from Table 21 that exhibited phase clarity and good to excellent solubility for Compound 1 were evaluated in monkey PK studies as shown in Table 22. In the table below, the % w/w are based on the total weight of the vehicle and compound. All six formulations were crash resistant. Maisine CC based formulations from Table 21 were not further evaluated due to relatively lower solubility of Compound 1 in these formulations. Caproyl based co-surfactant formulations were eliminated due to toxicity issues found with the excipient.

TABLE 22

Compositions of SEDDS Formulations Evaluated in Monkey PK Study

| Formulation # | Cmpd 1 (% wt/wt) | Solubilizer (% wt/wt) | Surfactant (% wt/wt) | Co-surfactant (% wt/wt) | Crash Resistant |
|---|---|---|---|---|---|
| 1 | 10.39 | Cottonseed oil (58.25) | Tween 80 (17.92) | Lauroglycol 90 (13.44) | Yes |
| 2 | 10.39 | Soybean oil (58.25) | Tween 80 (17.92) | Lauroglycol 90 (13.44) | Yes |
| 3 | 10.39 | Labrafac PG (58.25) | Tween 80 (17.92) | Lauroglycol 90 (13.44) | Yes |
| 4 | 10.39 | Olive oil (58.25) | Tween 80 (17.92) | Lauroglycol 90 (13.44) | Yes |
| 5 | 10.39 | Corn oil (58.25) | Tween 80 (17.92) | Lauroglycol 90 (13.44) | Yes |
| 6 | 10.39 | Labrafac WL 1349 (58.25) | Tween 80 (17.92) | Lauroglycol 90 (13.44) | Yes |

Three monkeys per group were evaluated and dosed with 50 mg/kg of Compound 1, in the respective formulations. The monkeys were fed 30 minutes prior to dosing with a medium fat liquid diet, 5 mL/kg containing 0.23 g/mL of total fat. Monkey PK study results are shown in FIG. 4a-4c. All of the SEDDS formulations were found to be orally bioavailable in monkeys and showed similar $T_{max}$ (Table 23). Most of the SEDDS formulations, including the Labrafac WL 1349-based formulation (Formulation 6), exhibited desirable PK profile, including the unexpected absence of a second peak. A second peak was observed with the sesame oil formulation and Formulation 4. In the first four hours, soybean, Labrafac PG, and Olive oil-based formulations showed a similar PK profile compared to the Labrafac WL 1349-based formulation (FIG. 5a-5c). Cottonseed oil-based formulation 1 showed the highest $C_{max}$ and AUC (FIGS. 5b and 5c).

The Labrafac WL 1349-based formulation showed the lowest PK variability and the desired plasma levels with minimal peak-to-trough ratio (difference between $C_{max}$ and $C_{trough}$), Table 23. The peak (bump) in the elimination phase observed with the sesame oil-only formulation and Formulation 4 was not observed with Formulations 1-3 and, 5, and 6.

TABLE 23

Monkey PK Study Results of SEDDS Formulations

| Group | Animal | $T_{1/2}$ hr | $T_{max}$ hr | $C_{max}$ | $AU_{Clast}$ |
|---|---|---|---|---|---|
| Formulation 1 | 1 | 8.8 | 4.0 | 3030 | 14593 |
| (Cottonseed | 2 | 10.0 | 4.0 | 2310 | 14177 |
| oil based) | 3 | 3.9 | 4.0 | 2070 | 6532 |
|  | Mean | 7.6 | 4.0 | 2470 | 11767 |
|  | SD | 3.3 | 0.0 | 500 | 4539 |
|  | % RSD | 43.1 | 0.0 | 20.2 | 38.6 |
| Formulation 2 | 4 | 6.8 | 4.0 | 1080 | 5014 |
| (Soybean oil | 5 | 9.9 | 4.0 | 1530 | 8430 |
| based) | 6 | 9.9 | 4.0 | 408 | 2147 |
|  | Mean | 8.9 | 4.0 | 1006 | 5197 |
|  | SD | 1.8 | 0.0 | 565 | 3146 |
|  | % RSD | 20.5 | 0.0 | 56.1 | 60.5 |
| Formulation 3 | 7 | 3.4 | 4.0 | 575 | 3402 |
| (Labrafac PG | 8 | 5.8 | 4.0 | 2070 | 7641 |
| based) | 9 | 4.9 | 4.0 | 1730 | 10991 |
|  | Mean | 4.7 | 4.0 | 1458 | 7345 |
|  | SD | 1.2 | 0.0 | 784 | 3803 |
|  | % RSD | 25.1 | 0.0 | 53.7 | 51.8 |
| Formulation 4 | 10 | 6.0 | 6.0 | 1480 | 10354 |
| (Olive oil | 11 | 4.0 | 2.0 | 1340 | 7180 |
| based) | 12 | 7.6 | 2.0 | 1230 | 8027 |
|  | Mean | 5.9 | 3.3 | 1350 | 8520 |
|  | SD | 1.8 | 2.3 | 125 | 1643 |
|  | % RSD | 30.7 | 69.3 | 9.3 | 19.3 |
| Formulation 5 | 13 | 9.6 | 4.0 | 2510 | 12584 |
| (Corn oil | 14 | 4.0 | 4.0 | 1410 | 6986 |
| based) | 15 | 4.8 | 6.0 | 1160 | 6665 |
|  | Mean | 6.2 | 4.7 | 1693 | 8745 |
|  | SD | 3.0 | 1.2 | 718 | 3329 |
|  | % RSD | 49.0 | 24.7 | 42.4 | 38.1 |
| Formulation 6 | 16 | 18.8 | 6.0 | 989 | 6079 |
|  | 17 | 7.3 | 4.0 | 772 | 4807 |
|  | 18 | 10.7 | 4.0 | 795 | 5967 |
|  | Mean | 12.3 | 4.7 | 852 | 5618 |
|  | SD | 5.9 | 1.2 | 119 | 704 |
|  | % RSD | 48.4 | 24.7 | 14.0 | 12.5 |

TABLE 23a

Monkey PK Study Results of SEDDS Formulations - Bioavailability

| Group | Animal | AUClast/D | AUCinf | AUCinf/D | AUC % extrap | F % |
|---|---|---|---|---|---|---|
| Formulation 1 | 1 | 292 | 14660 | 293 | 0.46 | 47 |
| (Cottonseed oil | 2 | 284 | 14284 | 286 | 0.75 | 45 |
| based) | 3 | 131 | 6570 | 131 | 0.58 | 21 |
| | Mean | 235 | 11838 | 237 | 0.60 | 38 |
| | SD | 90.8 | 4566 | 91.3 | 0.15 | 14 |
| | % RSD | 38.6 | 38.6 | 38.6 | 24.8 | 38.6 |
| Formulation 2 | 4 | 100 | 5066 | 101 | 1.03 | 16 |
| (Soybean oil | 5 | 169 | 8598 | 172 | 1.95 | 27 |
| based) | 6 | 42.9 | 2224 | 44.5 | 3.45 | 7 |
| | Mean | 104 | 5296 | 106 | 2.14 | 17 |
| | SD | 62.9 | 3193 | 63.9 | 1.22 | 10 |
| | % RSD | 60.5 | 60.3 | 60.3 | 56.9 | 60.3 |
| Formulation 3 | 7 | 68.0 | 3429 | 68.6 | 0.77 | 11 |
| (Labrafac PG | 8 | 153 | 7685 | 154 | 0.57 | 24 |
| based) | 9 | 220 | 11030 | 221 | 0.36 | 35 |
| | Mean | 147 | 7381 | 148 | 0.57 | 23 |
| | SD | 76.1 | 3810 | 76.2 | 0.21 | 12 |
| | % RSD | 51.8 | 51.6 | 51.6 | 36.8 | 51.6 |
| Formulation 4 | 10 | 207 | 10465 | 209 | 1.06 | 33 |
| (Olive oil based) | 11 | 144 | 7278 | 146 | 1.35 | 23 |
| | 12 | 161 | 8105 | 162 | 0.95 | 26 |
| | Mean | 170 | 8616 | 172 | 1.12 | 27 |
| | SD | 32.9 | 1654 | 33.1 | 0.21 | 5 |
| | % RSD | 19.3 | 19.2 | 19.2 | 18.3 | 19.2 |
| Formulation 5 | 13 | 252 | 12661 | 253 | 0.60 | 40 |
| (Corn oil based) | 14 | 140 | 7055 | 141 | 0.98 | 22 |
| | 15 | 133 | 6701 | 134 | 0.54 | 21 |
| | Mean | 175 | 8806 | 176 | 0.71 | 28 |
| | SD | 66.6 | 3343 | 66.9 | 0.24 | 11 |
| | % RSD | 38.1 | 38.0 | 38.0 | 34.0 | 38.0 |
| Formulation 6 | 16 | 122 | 6309 | 126 | 3.65 | 20 |
| | 17 | 96.1 | 4863 | 97.3 | 1.15 | 15 |
| | 18 | 119 | 6117 | 122 | 2.45 | 19 |
| | Mean | 112 | 5763 | 115 | 2.42 | 18 |
| | SD | 14.1 | 785 | 15.7 | 1.25 | 2 |
| | % RSD | 12.5 | 13.6 | 13.6 | 51.6 | 13.6 |

Certain formulation provided herein were tested for stability, as provided herein, and demonstrated good stability under various conditions. Other formulations, such as Formulations 1-5, provided herein, have not been tested for stability but would be expected to demonstrate comparable stability to those that were tested.

In certain embodiments, 20 wt/wt % Lauroglycol (wt/wt % based on total weight of vehicle) may advantageously assist in maintaining a one phase solution.

One advantage for Formulation 6 compared to a formulation of Compound 1 in sesame oil only is that Formula 6, with 10% w/w and 12% w/w Compound 1, are stable at RT, where the maximum advisable loading of Compound 1 in sesame oil only is 10% w/w. In addition, while the formulation of Compound 1 in sesame oil only demonstrated good chemical stability at RT, Formulation 6 demonstrated somewhat better chemical stability at accelerated conditions and for a longer term. Still another advantage of Formulation 6 compared to the formulation of Compound 1 in sesame oil only relates to micellization and solubilization in gastrointestinal fluids; Formulation 6 is designed to self-emulsify where sesame oil only formulation must rely on intestinal surfactants. Finally, the sesame oil formulation shows a 2.7-fold food effect (low fat to medium fat) where Formulation 6 shows a 1.96-fold food effect (low fat to medium fat).

Example 11

Manufacturability of Compound 1 Labrafac-WL-1349-Based Formulation Capsules (i). Viscosity of Labrafac-Based Formulation Vehicle A Brookfield viscometer with CP-51 spindle (Medium—High viscosity spindle) was calibrated. With highest 200 rpm (CP-51), Formulation D (Labrafac-WL-1349-based formulation vehicle with 15% Tween 80) has a viscosity of 23.56 cP. The acceptable viscosity for the encapsulation of the DP-vehicle mixing blend should be in between 0.222 and 3000 Cp.

(ii). Moisture Abstractability of Labrafac-WL-1349-Based Formulation Vehicle Components Moisture abstractability of the liquid formulation components in Hard Gelatin Capsule is shown in FIG. 6. The water equilibrium may be describe by the curves in FIG. 3 depending on the moisture/drying history. As long as the gelatin water content remains in the range of 11 to 16%, no significant effect is expected on capsules brittleness potential. Table 25 shows the analysis of individual components of Labrafac-WL-1349-based formulation on moisture ab stractability.

Both Labrafac-WL-1349 and Lauroglycol 90 have a very low potential to absorb moisture. While Tween 80 is hygroscopic, it is only 15% w/w in the vehicle and is not expected to influence the integrity of the capsule shell upon storage.

TABLE 25

Analysis of Individual Components of Labrafac-WL-1349-Based Formulation C-1 and D-1 on Moisture Abstractability

| Component | Formulation C-1 (20% Tween 80) % w/w | Formulation C-1 (20% Tween 80) mg/unit | Formulation D-1 (15% Tween 80) % w/w | Formulation D-1 (15% Tween 80) mg/unit | Description/Criteria | Risk level |
|---|---|---|---|---|---|---|
| Cmpd 1 | 10 | 50 | 10 | 50 | | NA |
| Labrafac Lipophile WL 1349 | 54 | 270 | 58.5 | 292.5 | Medium chain triglyceride of fractionated vegetable C8 and C10 fatty acids (mainly fractionated coconut oil or palm kernel oil) with an HLB of 1; non rancidable; no to very low hygroscopicity | Low |
| Lauroglycol 90 | 18 | 90 | 18 | 90 | Non-ionic water insoluble surfactant used as co-surfactant, consists of propylene glycol mono- and di-stearates of lauric acid (C12), with HLB value 3 | Low |
| Tween 80 | 18 | 90 | 13.5 | 67.5 | Polysorbates containing 20 units of oxyethylene are hydrophilic, hygroscopic, nonionic surfactants that are used as emulsifying agents | Med-High |

Example 12

Manufacturing Process for Oral Solution of Compound 1

Each of the oil, propylene glycol laurates composition (Lauroglycol 90), and polysorbate 80 (Tween 80) were weighed and added to a container, and were mixed until a uniform solution was formed. To this solution was added Compound 1. The resulting mixture was stirred until a yellow solution was obtained. The solution was then test visually and under microscope for the absence of Compound 1 crystals. The solution was filled in an amber glass bottle, closed and sealed with CRC cap. The optional flavorant can be added to either the mixture without Compound 1 or to the mixture containing Compound 1.

Example 13

Manufacturing Process for Semi Meal Procedure

Example 13a

Low Fat Meat (Containing 15% Calories from Fat)

The homogenized meal was prepared as follow: 30 g daily food (approximately 6% fat by weight) was weighed in a container. 90 mL water was added into the container and contents homogenized.

For low diet groups, animals were fasted overnight and given homogenized normal meal by gavage at 37.5 mL/animal (approximately 15 mL/kg) about 30 mins prior to dosing. The rest diet, approximately 90 g, was given to animals 4 hours post-dose.

Example 13b

Medium Fat Meat (Containing 38% Calories from Fat)

The homogenized meal was prepared as follow: 80 g of food weighed in a container. 15 mL eatable corn oil and some water were added into the container and placed it to soften them for about 30 min. Homogenized 20 min to mix well and made up the volume to 250 mL with water.

For medium diet groups, animals were fasted overnight and given homogenized normal meal by gavage at 37.5 mL/animal (approximately 15 mL/kg) about 30 mins prior to dosing. The rest diet (about 103 g), was given to animals 4 hours post-dose.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A pharmaceutical composition comprising:
a) about 48 wt/wt % to about 70 wt/wt % of a pharmaceutically acceptable oil, about 12 wt/wt % to about 25 wt/wt % of a propylene glycol laurates composition, and about 8 wt/wt % to about 20 wt/wt % of a polysorbate 80;
b) about 1 wt/wt % to about 15 wt/wt % of Compound 1:

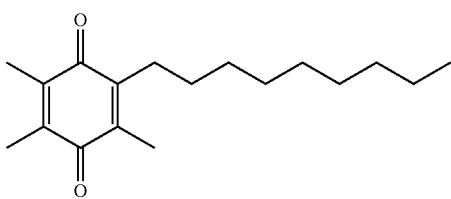 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 15 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, the propylene glycol laurates composition, the polysorbate 80, and optional flavorant total 100%.

2. The pharmaceutical composition of claim 1, comprising:

a) about 52 wt/wt % to about 65 wt/wt % of a pharmaceutically acceptable oil, about 17 wt/wt % to about 20 wt/wt % of a propylene glycol laurates composition, and about 13 wt/wt % to about 20 wt/wt % of a polysorbate 80;

b) about 1 wt/wt % to about 12 wt/wt % of Compound 1:

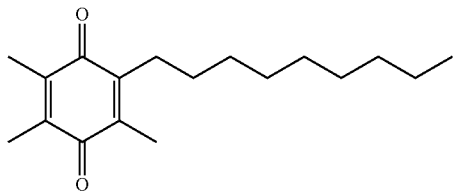 [SMILES: CCCCCCCCCC1=C(C)C(=O)C(C)=C(C)C1=O]

and/or the hydroquinone form thereof; wherein Compound 1, and/or the hydroquinone thereof is optionally a hydrate thereof, and/or solvate thereof; and wherein when Compound 1, and/or hydroquinone thereof, is in the form of a hydrate and/or solvate, then the about 1 wt/wt % to about 12 wt/wt % of Compound 1, and/or its hydroquinone, does not include the weight of the water in the hydrate or the weight of the solvent in the solvate; and c) 0 wt/wt % to about 2% wt/wt % of an optional flavorant;

wherein the wt/wt % of Compound 1, the pharmaceutically acceptable oil, the propylene glycol laurates composition, the polysorbate 80, and optional flavorant total 100%.

3. The pharmaceutical composition of claim 2, wherein the ratio of the pharmaceutically acceptable oil to propylene glycol laurates composition to polysorbate 80 is about 55-75 parts by weight of the pharmaceutically acceptable oil,
about 15-25 parts by weight of the propylene glycol laurates composition,
about 10-20 parts by weight of the polysorbate 80,
wherein the ratio is 55-75:15-25:10-20 by weight; and
wherein the parts in the ratio of the pharmaceutically acceptable oil to propylene glycol laurates composition to polysorbate 80 total 100.

4. The pharmaceutical composition of claim 2, wherein the ratio of the pharmaceutically acceptable oil to propylene glycol laurates composition to polysorbate 80 is about 60-65 parts by weight of the pharmaceutically acceptable oil,
about 20-25 parts by weight of the propylene glycol laurates composition,
about 15-20 parts by weight of the polysorbate 80,
wherein the ratio is 60-65:20-25:15-20 by weight; and
wherein the parts in the ratio of the pharmaceutically acceptable oil to propylene glycol laurates composition to polysorbate 80 total 100.

5. The pharmaceutical composition of claim 4, wherein the ratio of the pharmaceutically acceptable oil to propylene glycol laurates composition to polysorbate 80 is about 60 parts by weight of the pharmaceutically acceptable oil,
about 20 parts by weight of the propylene glycol laurates composition,
about 20 parts by weight of the polysorbate 80,
wherein the ratio is 60:20:20 by weight.

6. The pharmaceutical composition of claim 4, wherein the ratio of the pharmaceutically acceptable oil to propylene glycol laurates composition to polysorbate 80 is about 65 parts by weight of the pharmaceutically acceptable oil,
about 20 parts by weight of the propylene glycol laurates composition,
about 15 parts by weight of the polysorbate 80,
wherein the ratio is 65:20:15 by weight.

7. The pharmaceutical composition of claim 1, wherein the pharmaceutically acceptable oil is selected from the group consisting of one or more of: an oil of medium chain triglycerides, propylene glycol dicaprolate/dicaprate, sesame oil, cottonseed oil, soybean oil, olive oil, and corn oil; or selected from the group consisting of one or more of: an oil of medium chain triglycerides, propylene glycol dicaprolate/dicaprate, cottonseed oil, soybean oil, and corn oil; and optionally wherein one pharmaceutically acceptable oil is selected.

8. The pharmaceutical composition of claim 1, wherein the pharmaceutically acceptable oil is an oil of medium chain triglycerides, or propylene glycol dicaprolate/dicaprate.

9. The pharmaceutical composition of claim 1, wherein the pharmaceutically acceptable oil is sesame oil.

10. The pharmaceutical composition of claim 1, wherein the pharmaceutically acceptable oil is soybean oil.

11. The pharmaceutical composition of claim 1, wherein the pharmaceutically acceptable oil is an oil of medium chain triglycerides.

12. The pharmaceutical composition of claim 1, wherein the pharmaceutically acceptable oil is olive oil.

13. The pharmaceutical composition of claim 1, wherein the pharmaceutically acceptable oil is corn oil.

14. The pharmaceutical composition of claim 1, wherein the pharmaceutically acceptable oil is cottonseed oil.

15. The pharmaceutical composition of claim 1, wherein the propylene glycol laurates composition is propylene glycol monolaurate (type II).

16. The pharmaceutical composition of claim 1, wherein the polysorbate 80 is Tween 80.

17. The pharmaceutical composition of claim 1, wherein the pharmaceutical composition comprises about 1 wt/wt % to about 12 wt/wt %, about 4 wt/wt % to about 12 wt/wt %, or about 5 wt/wt % to about 10 wt/wt % of Compound 1.

18. The pharmaceutical composition of claim 1, wherein the pharmaceutical composition comprises about 5 wt/wt %, about 6 wt/wt %, about 7 wt/wt %, about 8 wt/wt %, about 9 wt/wt %, or about 10 wt/wt % of Compound 1.

19. The pharmaceutical composition of claim 1, wherein the pharmaceutical composition contains about 50 mg to about 120 mg of Compound 1 in the composition, about 50 mg to about 100 mg of Compound 1 in the composition, about 60 mg to about 100 mg of Compound 1 in the composition, about 100 mg to about 120 mg of Compound 1 in the composition, about 50 mg of Compound 1 in the composition, about 60 mg of Compound 1 in the composition, or about 100 mg of Compound 1 in the composition.

20. The pharmaceutical composition of claim 1, wherein b) is

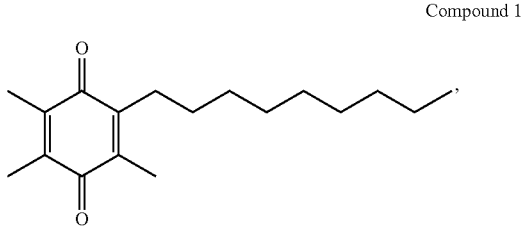 [SMILES: CCCCCCCCCC1=C(C)C(=O)C(C)=C(C)C1=O]

Compound 1 or one or more members selected from the group consisting of hydrates thereof and solvates thereof.

21. The pharmaceutical composition of claim 1, wherein b) is the hydroquinone form of

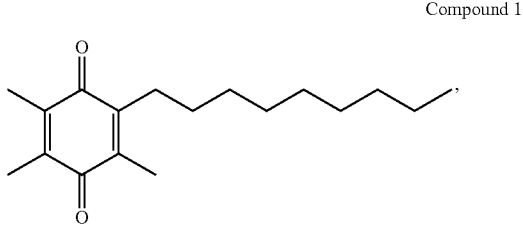 [SMILES: CCCCCCCCCC1=C(C)C(=O)C(C)=C(C)C1=O]

Compound 1 or one or more members selected from the group consisting of hydrates thereof, and solvates thereof.

22. The pharmaceutical composition of claim 1, wherein the pharmaceutical composition is an oral pharmaceutical composition and wherein oral bioavailability for Medium-fat Food for Testing is about 45% to about 55%, about 40 to about 50%, about 49%; optionally wherein the pharmaceutically acceptable oil is an oil of medium chain triglycerides, the propylene glycol laurates composition is propylene glycol monolaurate (type II), and the polysorbate 80 is Tween 80; additionally optionally wherein the ratio by weight of the oil of medium chain triglycerides to the propylene glycol monolaurate (type II) to the polysorbate 80 is about 60:20:20.

23. The pharmaceutical composition of claim 22, wherein oral bioavailability for Low-fat Food for Testing is about 10% to about 15%, in some embodiments, about 13%; optionally wherein the pharmaceutically acceptable oil is an oil of medium chain triglycerides, the propylene glycol laurates composition is propylene glycol monolaurate (type II), and the polysorbate 80 is Tween 80; additionally optionally wherein the ratio by weight of the pharmaceutically acceptable oil to the propylene glycol laurates composition to the polysorbate 80 is about 60:20:20.

24. The pharmaceutical composition of claim 1, wherein the pharmaceutical composition is an oral pharmaceutical composition and wherein oral bioavailability for Medium-fat Food for Testing is about 15% to about 40%, 25% to about 35%, about 29%; optionally wherein the ratio by weight of the pharmaceutically acceptable oil to the propylene glycol laurates composition to the polysorbate 80 is about 65:20:15; and additionally optionally wherein the pharmaceutically acceptable oil is an oil of medium chain triglycerides, propylene glycol dicaprolate/dicaprate, cottonseed oil, soybean oil, olive oil, or corn oil; the propylene glycol laurates composition is propylene glycol monolaurate (type II); and the polysorbate 80 is Tween 80.

25. The pharmaceutical composition of claim 24, wherein oral bioavailability for Low-fat Food for Testing is about 10% to about 15%, in some embodiments, about 14%; optionally wherein the pharmaceutically acceptable oil is an oil of medium chain triglycerides, the propylene glycol laurates composition is propylene glycol monolaurate (type II), and the polysorbate 80 is Tween 80; additionally optionally wherein the ratio by weight of the pharmaceutically acceptable oil to the propylene glycol laurates composition to the polysorbate 80 is about 65:20:15.

26. A method of preparing a pharmaceutical composition of claim 1, comprising:
step a) mixing about 48 wt/wt % to about 70 wt/wt % of a pharmaceutically acceptable oil, about 12 wt/wt % to about 25 wt/wt % of a propylene glycol laurates composition, about 8 wt/wt % to about 20 wt/wt % of a polysorbate 80, and 0 wt/wt % to about 2% wt/wt % of an optional flavorant;
step b) adding about 1 wt/wt % to about 15%, of Compound 1 and/or the hydroquinone form thereof, wherein Compound 1 and/or the hydroquinone form thereof is optionally a hydrate and/or solvate thereof; to the mixture from step a) and mixing,
and wherein when the Compound 1, and/or hydroquinone thereof, is in the form of a hydrate and/or solvate, then the about 1 wt/wt % to about 15 wt/wt % of Compound 1 and/or its hydroquinone, does not include the weight of any the water in the hydrate or the weight of the solvent in the solvate; and
wherein the wt/wt % of Compound 1, the pharmaceutically acceptable oil, the propylene glycol laurates composition, the polysorbate 80, and optional flavorant total 100%.

27. A method for treating or suppressing a disease or disorder selected from the group consisting of an α-synucleinpathy, a tauopathy, an autistic spectrum disorder, a pervasive developmental disorder, a liver disease, liver damage, dementia, and reperfusion injury, comprising administering a pharmaceutical composition of claim 1.

28. The method of claim 27, wherein the pharmaceutical composition is administered at a dose selected from 150 mg BID and 250 mg BID.

29. The method of claim 27, wherein the pharmaceutical composition is administered at a dose ranging from about 100 mg to about 1000 mg daily dose for a period of at least 14 days.

* * * * *